(12) United States Patent
Ekwuribe et al.

(10) Patent No.: US 6,703,381 B1
(45) Date of Patent: Mar. 9, 2004

(54) METHODS FOR DELIVERY THERAPEUTIC COMPOUNDS ACROSS THE BLOOD-BRAIN BARRIER

(75) Inventors: Nnochiri N. Ekwuribe, Cary, NC (US); Balasingam Rhadakrishnan, Chapel Hill, NC (US); Christopher H. Price, Chapel Hill, NC (US); Wes Anderson, Jr., Raleigh, NC (US); Aslam M. Ansari, Durham, NC (US)

(73) Assignee: Nobex Corporation, Durham, NC (US)

( * ) Notice: Subject to any disclaimer, the term of this patent is extended or adjusted under 35 U.S.C. 154(b) by 0 days.

(21) Appl. No.: 09/134,803

(22) Filed: Aug. 14, 1998

(51) Int. Cl.$^7$ .............................................. A61K 31/56
(52) U.S. Cl. ...................................... 514/182; 435/188
(58) Field of Search ........................... 514/26, 178, 182, 514/3, 4, 12, 21; 435/188; 500/303, 307, 324–26, 309, 345, 322, 402, 409–11, 375, 351

(56) References Cited

U.S. PATENT DOCUMENTS

| | | |
|---|---|---|
| 3,256,153 A | 6/1966 | Heimlich |
| 4,003,792 A | 1/1977 | Mills et al. |
| 4,044,196 A | 8/1977 | Hüper et al. |
| 4,179,337 A | 12/1979 | Davis et al. |
| 4,410,547 A | 10/1983 | Ueno et al. |
| 4,537,878 A * | 8/1985 | Plotnikoff |
| 4,585,754 A | 4/1986 | Meisner et al. |
| 4,622,392 A | 11/1986 | Hong et al. |
| 4,684,524 A | 8/1987 | Eckenhoff et al. |
| 4,698,264 A | 10/1987 | Steinke |
| 4,717,566 A | 1/1988 | Eckenhoff et al. |
| 4,744,976 A | 5/1988 | Snipes et al. |
| 4,772,471 A | 9/1988 | Vanlerberghe et al. |
| 4,797,288 A | 1/1989 | Sharma et al. |
| 4,840,799 A | 6/1989 | Appelgren et al. |
| 4,849,405 A | 7/1989 | Ecanow |
| 4,935,246 A | 6/1990 | Ahrens |
| 4,939,174 A | 7/1990 | Shashoua |
| 4,963,367 A | 10/1990 | Ecanow |
| 5,013,556 A | 5/1991 | Woodle et al. |
| 5,055,300 A | 10/1991 | Gupta |
| 5,055,304 A | 10/1991 | Makino et al. |
| 5,093,198 A | 3/1992 | Speaker et al. |
| 5,286,637 A | 2/1994 | Veronese et al. |
| 5,539,063 A | 7/1996 | Hakimi et al. |
| 5,545,719 A | 8/1996 | Shashoua et al. |
| 5,559,213 A | 9/1996 | Hakimi et al. |
| 5,571,795 A * | 11/1996 | Kahne et al. ................ 514/26 |
| 5,595,732 A | 1/1997 | Hakimi et al. |
| 5,602,099 A | 2/1997 | Schiller |
| 5,631,263 A | 5/1997 | Portoghese et al. |
| 5,641,861 A | 6/1997 | Dooley et al. |
| 5,653,987 A | 8/1997 | Modi et al. |
| 5,663,295 A | 9/1997 | Moreau et al. |
| 5,681,811 A * | 10/1997 | Ekwuribe et al. |
| 5,693,769 A * | 12/1997 | Kahne et al. |
| 5,747,646 A | 5/1998 | Hakimi et al. |
| 5,786,447 A | 7/1998 | Schiller et al. |
| 5,792,834 A | 8/1998 | Hakimi et al. |
| 5,932,462 A | 8/1999 | Harris et al. ................ 435/188 |

FOREIGN PATENT DOCUMENTS

| | | |
|---|---|---|
| WO | WO93/01802 | 2/1993 |

OTHER PUBLICATIONS

Mosnaim et al., "Studies of the In Vitro Human Plasma Degradation of Methionine–Enkephalin," Gen. Pharmac., 1988, vol. 19, No. 5, p. 729–733.*

Chun., W., et al., "Transmucosal Delivery of Methionine Enkephalin. I: Solution Stability and Kinetics of Degradation in Various Rabbit Mucosa Extracts," J. Pharm.Sci., 1993, 82 (4), pp: 373–378.

Brewster, M.E., et al., "Efficacy of a 3–Substituted Versus 17–Substiturted Chemical Delivery System for Estradiol Brain Targeting," J. Pharm. Sci., 1994, pp: A–E.

Mosnaim, A.D., et al., "Studies of the in Vitro Human Plasma Degradation of Methionine–Enkephalin," Gen. Pharmac., 1988, 19 (5), pp: 729–733.

Weber, S.J., et al., "Distribution and Analgesia of [$^3$H] [D–PEN$^2$, D–PEN$^5$] Enkephalin and Two Halogenated Analogs after Intravenous Administration," J. Pharm. Exper. Ther., 1991, 259, pp: 1109–1112.

Brewster, M.E., et al., "Effect of Molecular Manipulation on the Estrogenic Activity of a Brain–Targeting Estradiol Chemical Delivery System," J. Med. Chem., 1994, 37, pp: 4237–4244.

Pardridge, W.M., "New Approaches to Drug Delivery Through the Blood–Brain Barrier," Trends in Biotechnology, 1994, pp: 239–245.

Shashoua, V.E., et al., "N–Docosahexaenoyl, 3 Hydroxytyramine: A Dopaminergic Compound that Penetrates the Blood–Brain Barrier and Suppresses Appetite," Life Sciences, 58 (16), pp: 1347–1354.

Gibson, A.M., et al., "Specificity of Action of Human Brain Alanyl Aminopeptidase on Leu–Enkephalin and Dynorphin–Related Peptides," Neuropeptides, 1989, 13, pp: 259–262.

(List continued on next page.)

*Primary Examiner*—Ralph Gitomer
(74) *Attorney, Agent, or Firm*—Myer Bigel Sibley & Sajovec, P.A.; William A. Barrett, Esq.

(57) ABSTRACT

The present invention relates to amphiphilic drug-oligomer conjugates capable of traversing the blood-brain barrier ("BBB") and to methods of making and using such conjugates. An amphiphilic drug-oligomer conjugates comprise a therapeutic compound conjugated to an oligomer, wherein the oligomer comprises a lipophilic moiety coupled to a hydrophilic moiety. The conjugates of the invention further comprise therapeutic agents such as proteins, peptides, nucleosides, nucleotides, antiviral agents, antineoplastic agents, antibiotics, etc., and prodrugs, precursors, derivatives and intermediates thereof, chemically coupled to amphiphilic oligomers.

16 Claims, 11 Drawing Sheets

OTHER PUBLICATIONS

Figure 1A:
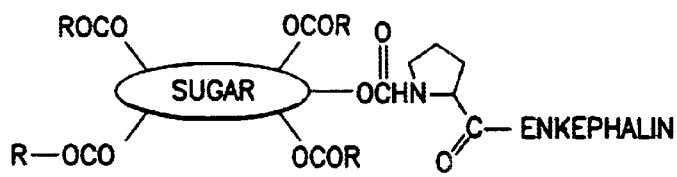

Prokai–Tatrai, K., et al., "Brain–Targeted Delivery of a Leucine–Enkephalin Analogue by Retrometabolic Design," J. Med. Chem, 1996, 39 (24).

Conradi, R.A., et al., "The Influence of Peptide Structure on Transport Across Caco–2 Cells," Pharm. Res., 1991, 8 (12): pp. 1453–1459.

Boccu, E. et al., "Pharmocokinetic Properties of Polyethylene Glycol Derivatized Superoxide Dismutase," Pharm. Res. Comm., 1982, 14: pp. 11–120.

Igarashi, R. et al., "Biologically Active Peptides Conjugated with Lecithin for DDS" Proceed. Intern. Symp. Cont. Rel. Bioactiv. Mater. 1990, 17: pp. 367–368.

Taniguchi, T. et al., "Synthesis of Acyloyl Lysozyme and Improvement of its Lymphatic Transport Following Small Intestinal Administration in Rats," Proceed. Intern. Symp. Control. Rel. Bioactiv. Mater., 1992, 19: pp. 104–105.

Russell–Jones, G. J., "Vitamin B12 Drug Delivery," Proceed. Intern. Symp. Control. Rel. Bioactive. Mater., 1992, 19: pp. 102–103.

Baudys, M. et al., "Synthesis and Characteristics of Different Glycosylated Derivatives of Insulin," Proceed. Intern. Symp. Cont. Rel. Bioactiv. Mater., 1992, 19: pp. 210–211.

Chien, Y.W., Novel Drug Delivery Systems, pp. 678–679, Marcell Deffer, Inc., New York, NY, 1992.

Pardridge, W.M., "CNS Drug Design Based on Principles of Blood–Brain Barrier Transport," J. Neurochem., 1998, 70 (5): pp. 1781–1792.

Kroll, R.A., et al., "Outwitting the Blood–Brain Barrier for Therapeutic Purposes: Osmotic Opening and Other Means," 1998 Neurosurgery, 42 (5): pp. 1083–1100.

Pardridge, W.M., "Blood–Brain Barrier Peptide Transport and Peptide Drug Delivery to the Brain," Amer. Chem Soc. 1995, pp: 265–296.

Banks, W.A., et al., "Passage of Peptides Across the Blood–Brain Barrier: Pathophysiological Perspectives," Life Sciences, 1996, 59 (23), pp: 1923–1943.

Fix, J.A., "Oral Controlled Release Technology for Peptides: Status and Future Prospects," Pharm. Res., 1996, 13 (12): pp: 1760–1763.

Terasaki, T., et al., "Oligopeptide Drug Delivery to the Brain," Amer. Chem. Soc. 1995, pp: 297–316.

Bodor, N., et al., "Molecular Packaging. Peptide Delivery to the Central Nervous System by Sequential Metabolism," Amer. Chem. Soc., 1995, p:317–337.

Nestor, J., "Improved Duration of Action of Peptide Drugs," Amer. Chem Soc. 1995, pp:449–471.

Santiago, N. et al., "Oral Immunization of Rats with Influenze Virus M Protein (M1) Microspheres," Proceed. Intern. Symp. Cont. Rel. Bioactiv. Mater., 1992, 19: pp. 116–117.

Banting, R. G., et al., "Pancreatic Extracts in the Treatment of Diabetes Mellitus," The Canadian Med. Assoc. J. 1922, 12: pp. 141–146.

Brange, J. et al., "Chemical Stability of Insulin. 1. Hydrolytic Degradation During Storage of Pharmaceutical Preparations," Pharm. Res., 1992, 9 (6): pp. 715–726.

Nucci, et al., "The Therapeutic Value of Poly(ethylene glycol)—Modified Proteins," Ac. Drug. Del. Rev. 1991, 6: pp. 133–151.

Brange, J. et al., "Chemical Stability of Insulin. 2. Formation of Higher Molecular Weight Transformation Products During Storage of Pharmaceutical Preparations," Pharm. Res., 1992, 9 (6): pp. 727–734.

Robbins, D. C. et al., "Antibodies to Covalent Aggregates of Insulin in Blood of Insulin–Using Diabetic Patients," Diabetes, 1987, 36: pp. 838–841.

Maislos, M. et al., "The Source of the Circulating Aggregate of Insulin in Type I Diabetic Patients is Therapeutic Insulin," J. Clin. Invest., 1986, 77: pp. 717–723.

Ratner, R. E. et al., "Persistent Cutaneous Insulin Allergy Resulting from High–Molecular Weight Insulin Aggregates," Diabetes, 1990, 39: pp. 728–733.

Oka, K. et al., "Enhanced Intestinal Absorption of a Hydrophobic Polymer–Conjugated Protein Drug, Smancs, in an Oily Formulation," Pharm. Res., 1990, 7 (8): pp. 852–855.

Saffran, M. et al., "A New Approach to the Oral Administration of Insulin and Other Peptide Drugs," Science, 1986, 233: pp. 1081–1084.

Abuchowski, A. and F. F. Davis, "Soluble Polymer–Enzyme Adducts," pp. 368–383, Enzymes as Drugs, J. S. Holcenberg, John Wiley, 1981.

Akiyama, M. et al., "The Synthesis of New Derivatives of 1–β–D–Arabinofuranosylcytosine," Chem. Pharm. Bull., 1978, 26(3): p. 981.

Gish, D. T. et al., "Nucleic Acids. 11. Synthesis of 5'–Esters of 1–β–D–Arabinofuranosylcytosine Possessing Antileukemic and Immunosuppressive Activity," J. Med. Chem., 1971, 14(12): pp. 1159–1162.

Baker, D. C. et al., "Prodrugs of 9–β–D–Arabinofuranosyladenine. 1. Synthesis and Evaluation of Some 5'–(O–Acyl) Derivatives," J. Med. Chem., 1978, 21(12): pp. 1218–1221.

Hostetler, K. Y. et al., "Synthesis and Antiretroviral Activity of Phospholipid Analogs of Azidothymidine and Other Antiviral Nucleosides," The Journal of Biological Chemistry, 1990, 265(11): pp. 6112–6117.

Hong, C. I. et al., "Nucleoside Conjugates. 7. Synthesis and Antitumor Activity of 1–β–D–Arabinofuranosylcytosine Conjugates of Ether Lipids," J. Med. Chem., 1986, 29: pp. 2038–2044.

Aoshima, M. et al., "$N^4$–Behenoyl–1–β–D– Arabinofuransylcytosine as a Potential New Antitumor Agent," Cancer Research, 1977, 37: pp. 2481–2486.

Zalipsky, S. et al., "Attachment of Drugs to Polyethylene Glycols," Eur. Polym. J., 1983, 19(12): pp. 1177–1183.

Tsuzuki, N., et al., "Rabid Communication. Adamantane as a Brain–Directed Drug Carrier for Poorly Absorbed Drug: Antinociceptive Effects of [D–Ala$^2$] Leu–Enkephalin Derivatives Conjugated with the 1–Adamantane Moiety," Biochemical Pharmacology, 1991, 41 (4): pp. R5–R8.

Wagner, J., et al., "Neuropharmacology of Endogenous Opioid Peptides," Psychopharmacology: The Fourth Generation of Progress, 1995, pp: 519–529.

Horvat, J., et al., "Synthesis and Biological Activity of [Leu$^5$] Enkephalin Derivatives Containing D–Glucose," J. Peptide Protein Res., 1988, 31, pp: 499–507.

Shashoua V.E., et al., "γ–Aminobutyric Acid Esters. 1. Synthesis, Brain Uptake, and Pharmacological Studies of Aliphatic and Steroid Esters of γ–Aminobutyric Acid," J. Med. Chem., 1984, 27 (5), pp: 660–664.

Brewster, M., et al., "Tissue Distribution of LY231617, an Antioxidant with Neuroprotectant Activity, in the Rat," J. Pharm. Studies, 1995, 84 (7), pp: 791–793.

Chen, C., et al., "Extensive Biliary Excretion of the Model Opioid Peptide [D–PEN$^{2,5}$] Enkephalin in Rats," Pharm. Res. J., 14, pp: 345–350.

Bodor, N., et al., "A Strategy for Delivering Peptides into the Central Nervous System by Sequential Metabolism," Science, 1992, 257, pp: 1698–1702.

Sim, L., et al., "In vitro Autoradiography of Receptor–Activiated G Proteins in Rat Brain by Agonist–stimulated Guanylyl 5'–[γ[$^{35}$S]thio]–Triphosphate Binding," Proc. Natl. Acad. Sci., USA, 1995, 92, pp: 7242–7246.

Weber, S.J., et al., "Whole Body and Brain Distribution of [$^3$H]Cyclic [D–PEN$^2$, D–PEN$^5$] Enkephalin after Intraperitoneal, Intravenous, Oral and Subcutaneous Administration," J. Pharm. Exper. Ther., 1992, 263 pp: 1308–1316.

Alyautdin, R.N., "Delivery of Loperamide Across the Blood–Brain Barrier with Polysorbate 80–Coated Polybutylcyanoacrylate Nanoparticles," Pharm. Res. J., 1997, 14, pp: 325–328.

Chiou, G.C.Y., et al., "Systemic Delivery of Enkephalin Peptide through Eyes," Life Sciences, 1988, 43, pp: 509–514.

Sakaeda, T., et al., "Conjugation with L–Glutamic Acid for Brain Drug Delivery," Proceed. Intern. Symp. Control. Rel. Bioact. Mater., 1966, 23, pp: 607–608.

Delgado et al. "The Uses and Properties of PEG–Linked Proteins". *Critical Review in Therapeutic Drug Carrier Systems*, 9(3, 4):249–304 (1992).

* cited by examiner

SUGAR-CONTAINING AMPHIPHILIC OLIGOMERS

COMPARISON OF μ-RECEPTOR BINDING AFFINITY OF ENKEPHALIN CONJUGATES

| DRUG OR CONJUGATE | DETAILED STRUCTURE | % SPECIFIC BINDING |
|---|---|---|
| NALOXONE | NALOXONE | 100 |
| ENKEPHALIN | MET-ENKEPHALIN-LYS (SEQ ID NO: 49) | 67 |
| CETYL-ENK | CETYL-PEG$_2$-ENK (SEQ ID NO: 1) | 100 |
| CHOL-ENK | CHOLESTEROL-PEG$_3$-ENK (SEQ ID NO: 1) | 95 |
| DHA-ENK | DHA-PEG$_2$-ENK (SEQ ID NO: 1) | 63 |
| PALM-ENK | PALMITATE-PEG$_3$-ENK (SEQ ID NO: 1) | 76 |
| CETYL-TEG-ENK | CETYL-PEG$_3$-ENK (SEQ ID NO: 1) | 100 |

FIG.8

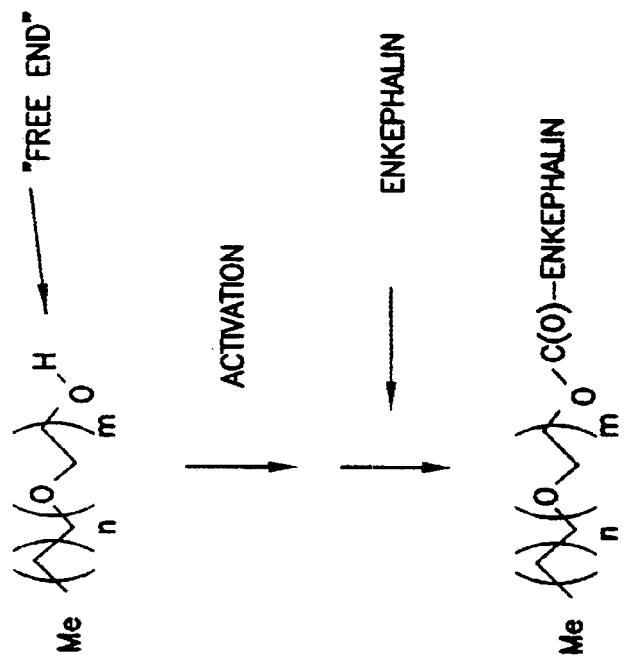

METHODS FOR DELIVERY THERAPEUTIC COMPOUNDS ACROSS THE BLOOD-BRAIN BARRIER

BACKGROUND OF THE INVENTION

1.1 Field of the Invention

The present invention relates to amphiphilic oligomer conjugates capable of traversing the blood-brain barrier ("BBB") and to methods of making and using such conjugates. The conjugates of the invention comprise therapeutic agents such as proteins, peptides, nucleosides, nucleotides, antiviral agents, antineoplastic agents, antibiotics, etc., and prodrugs, precursors, derivatives and intermediates thereof, chemically coupled to amphiphilic oligomers.

1.2 Description of the Related Art

In the field of pharmaceutical and therapeutic invention and the treatment of disease states and enhancement of physiological conditions associated with the CNS, a wide variety of therapeutic agents have been developed, including proteins, peptides, nucleosides; nucleotides, antiviral agents, antineoplastic agents, antibiotics, etc., and prodrugs, precursors, derivatives and intermediates thereof.

Additionally, the many known neuroactive peptides offer additional possibilities for useful therapeutic agents. Such neuroactive peptides play important biochemical roles in the CNS, for example as neurotransmitters and/or neuromodulators. Delivery of this diverse array of peptides to the CNS provides many opportunities for therapeutic benefit. For example, delivery of endogenous and synthetic opioid peptides, such as the enkephalins, can be used to effect analgesia.

However, a number of obstacles currently limit the use of many compounds for use as CNS therapeutic agents.

First, the brain is equipped with a barrier system. The brain barrier system has two major components: the choroid plexus and the blood-brain barrier (BBB). The choroid plexus separates cerebrospinal fluid (CSF) from blood and the BBB separates brain ISF from blood.

The BBB has about 1000 times more surface area than the choroid plexus and is the primary obstacle to delivery of therapeutic compounds to the CNS. The BBB acts as a selective partition, regulating the exchange of substances, including peptides, between the CNS and the peripheral circulation. The primary structure of the BBB is the brain capillary endothelial wall. The tight junctions of brain capillary endothelial cells prevent circulating compounds from reaching the brain ISF by the paracellular route. Furthermore, recent work suggests the existence of a physiological barrier at the level of the basal lamina, in addition to the barrier provided by the tight junctions. Kroll et al., *Neurosurgery*, Vol. 42, No. 5, p.1083 (May 1998). Other unique characteristics of the BBB include lack of intracellular fenestrations and pinocytic vesicles and a net negative charge on the luminal surface of the endothelium. Id.

The mechanisms by which substances may traverse the BBB may generally be divided into active and passive transport mechanisms. Lipophilic molecules readily traverse the BBB by passive transport or diffusion through the endothelial plasma membranes. In contrast, hydrophilic molecules, such as peptides, typically require Ian active transport system to enable them to cross the BBB. Certain larger peptides, such as insulin, have receptors on the luminal surface of the brain capillaries which act as active transcytosis systems.

Diffusion of many therapeutic compounds, such as peptides, across the BBB is also inhibited by size. For example, cyclosporin, which has a molecular weight of ~1200 Daltons (Da), is transported through the BBB at a much lower rate than its lipid solubility would predict. Such divergence between lipid solubility and BBB permeation rates is probably due to steric hindrances and is common where the molecular weight of a compound exceeds 800–1000 Da.

A further barrier to peptide delivery to the CNS is metabolic instability. In particular, before peptides injected into the blood reach the CNS, they must survive contact with enzyme degrading enzymes in the blood and in the brain capillary endothelium. BBB enzymes are known to degrade most naturally occurring neuropeptides. Orally administered peptides face additional barriers discussed below. Metabolically stabilized peptides may exhibit increased resistance to certain enzymes; however, it has not been possible to protect peptides from the wide range of peptide-degrading enzymes present in the blood and BBB.

Another difficulty inherent in delivering peptides to the BBB is that successful transcytosis is a complex process which requires binding at the lumenal or blood side of the brain capillary endothelium, movement through the endothelial cytoplasm, and exocytosis at the ablumenal or brain side of the BBB. Peptides may bind to the lumenal membrane of the brain capillary endothelium or undergo binding and endocytosis into the intracellular endothelial compartment without being transported into the CNS.

In any event, many currently existing drug substances, especially peptides, are unable to overcome these structural and metabolic barriers to enter the BBB in sufficient quantities to be efficacious. There is therefore a need for pharmaceutical compositions which can (1) withstand degradative enzymes in the blood stream and in the BBB and (2) which can penetrate through the BBB in sufficient amounts and at sufficient rates to be efficacious.

Many attempts have been made in the art to deliver therapeutic compounds, such as peptides, to the CNS with varying levels of success. Such attempts can generally be grouped into two categories: invasive and pharmacological.

Invasive delivery strategies include, for example, mechanical procedures, such as implantation of an intraventricular catheter, followed by pharmaceutical infusion into the ventricular compartment. Aside from general considerations relating to the invasiveness of mechanical procedures, a major difficulty with mechanical approaches is the lack of peptide distribution. For example, injection of peptides into the CSF compartment results in very little distribution beyond the surface of the brain. This lack of distribution is due in part to rapid exportation of peptides to the peripheral circulation.

Another invasive strategy for delivering therapeutic compounds to the CNS is by intracartoid infusion of highly concentrated osmotically active substances, such as mannitol or arabinose. Their high local concentration causes shrinkages of the brain. capillary endothelial cells, resulting in a transient opening of the tight junctions which enable molecules to traverse the BBB. Such procedures have considerable toxic effects, including inflammation, encephalitis, etc. Furthermore, such procedures are not selective: the opening of the tight junctions of the BBB permits many undesirable substances to cross the BBB along with the therapeutically beneficial molecule. For a recent review of osmotic opening and other invasive means for traversing the BBB, see Kroll, Robert A. *Neurosurgery*, Vol. 42, No. 5, May 1998.

While the risks involved in these invasive procedures maybe justified for life-threatening conditions, they are generally not acceptable for less dramatic illnesses. There is therefore a need for less invasive, non-mechanical and safer means for enabling therapeutic compounds to cross the BBB.

As noted above, lipophilic substances can generally diffuse freely across the BBB. Accordingly, a common pharmacological strategy for enabling peptides to traverse the BBB is to chemically modify the peptide of interest to make it lipid-soluble. Hydrophilic drug substances have been derivatized with short chain or long chain fatty acids to form prodrugs with increased lipophilicity.

Prodrugs are biologically inert molecules which require one or more metabolic steps to convert them into an active form. A difficulty with the prodrug approach to crossing the BBB is that the cleavage necessary to yield an active drug may not occur with sufficient efficiency and accuracy to produce an efficacious amount of the drug.

There is therefore a need for modified stable therapeutic compounds, such as peptides, which are capable of traversing the BBB but which retain all or part of their efficacy without requiring metabolic steps to convert them into an active form.

A further difficulty with lipidized prodrugs is that they pass in and out of the CNS so readily that they may never reach sufficient concentration in the CNS to achieve their intended function. For example, previous attempts have been made to engineer enkephalin conjugates which can traverse the BBB. See Partridge, W. M., "Blood-Brain Barrier Transport and Peptide Delivery to the Brain," *Peptide-Based Drug Design: Controlling Transport and Metabolism*, p. .277 (1995). However, these strategies required the subcutaneous delivery of frequent and massive doses of peptide to induce analgesia. Frequent and/or massive dosing is inconvenient to the patient and may result in serious side effects.

There is therefore a need in the art for means for enabling therapeutic agents, such as peptides, to cross the BBB in a controlled manner which permits accumulation of sufficient quantities of the therapeutic in the brain to induce the desired therapeutic effect.

Another pharmacological method for delivering peptides across the BBB is to covalently couple the peptide of interest to a peptide for which a specific receptor-mediated transcytosis system exists. ° For example, it is theoretically possible to attach β-endorphin, which is not normally transported through the BBB, to insulin to be transported across the BBB by insulin receptor-mediated transcytosis. Upon entry into the brain interstitial space, the active peptide (β-endorphin) is then released from the transport vector (insulin) to interact with its own receptor.

However, the difficulty with this system is designing a chimeric molecule which can become detached upon entry into the interstitial space; to the inventor's knowledge, this has not yet been achieved. Additionally, the poor stoichiometry of the neuropeptide to the carrier molecule limits the mass of the target peptide. Furthermore, receptor-mediated cellular transport systems typically have physiologically limited transport capacity. This is a rate-limiting factor which can prevent entry of pharmaceutically active amounts of-peptide.

There is therefore a need in the art for means for enabling therapeutic substances, such as peptides, to cross the BBB by diffusion so as to avoid the limitations inherent in receptor-mediated transport.

Other pharmacological strategies 7include using an active fragment of a native peptide; modification of a native peptide to increase blood-brain barrier (BBB) transport activity; and delivery of a gene encoding the neuropeptide to the brain.

Oral administration is a desirable and convenient route of administration; however, orally delivered peptides must overcome a series of barriers before they can enter the blood stream. Such peptides must survive proteolysis and the acidic environment of the stomach, gastric and pancreatic enzymes, exo- and endopeptidases in the intestinal brush border membrane.

There is therefore a need for orally administered peptides which can also resist proteolytic enzymes in the blood and BBB and which can traverse the BBB in sufficient quantities to provide broad distribution of drugs into the entire brain parenchyma.

Methionine-enkephalin and leucine-enkephalin are naturally occurring analgesic pentapeptides. These peptides and their analogs are known to-act as neurotransmitters or modulators in pain transmission. Their analgesic properties are short in duration. When administered by intracerebroventricular injection, the duration of their action is also transient.

These properties make the enkephalins attractive compounds for use as therapeutic agents, for mediating analgesia and providing a viable alternative to morphine. However, in order to deliver enkephalkins across the BBB, they must be protected against rapid degration by aminopeptidases and enkephalinases. Furthermore, since enkephalins are hydrophilic peptides, they must be modified to provide them with increased lipophilic characteristics before they can passively diffuse across the BBB into the CNS.

The attractive therapeutic properties of enkephalins have been known for sometime, and many investigators have attempted to enhance the ability of enkephalins to traverse the BBB.

Schroder et al., *Proc. Int. Symp. Control Rel. Biact. Material*, Vol. 23, p 611 (1996) teaches that Dalargin, a leu-enkephalin analogue can be incorporated in nanoparticles formed by polymerization of butylanoacrylate. The particles are coated with polysorbate, a penetration enhancer. Analgesic activity is obtained after intravenous administration. Unlike the present invention, however, the Schroder peptide must be chemically-bound to the polymeric material or to the polysorbate. The formulation is therefore a physical mixture of active drug and polymeric material.

Tsuzuki et al., Biochem. Pharm. Vol. 41, p. R5 (1991) teaches that analogues of leuenkephalin can be derivatized with adamantane moiety to obtain lipophilic enkephalin that shows an antinociceptive effect after subcutaneous administration. Modification at the N-terminus abolishes activity while the derivative at the C-terminus through ester bond retains activity. It is postulated that the activity is obtained after cleavage of the adamantane moiety. The derivative is therefore a prodrug, a concept not consistent with aspects of the present invention in which the-therapeutic conjugate retains the activity of the native peptide.

Prokai-Tatra, *J. M. Chem*, Vol. 39, p. 4777 (1996) teaches that a leucine-enkephalin analogue can be modified with chemical delivery system which is based on a retrometabolic drug design. The enkephaklin analogue is derivatized with a dihydropyridine moiety at the N-terminus and a lipophilic moiety at the C-terminus. After intravenous administration of the conjugate, analgesic response is observed. It is postulated that the lipophilic modification at the C-terminus enables penetration into the CNS, while the dihydropyridine moiety undergoes oxidative transformation to generate a charged moiety which restricts the peptides from effluxing into the circulatory system. Cleavage of the peptide from this moiety restores the observed analgesic activity. The derivatized peptide is inactive and regains activity only after metabolic transformation. The product is therefore a pure prodrug, requiring metabolic transformation to transform it into an active form.

U.S. Patent 4,933,324 to Shashoua teaches that certain natural fatty acids can be conjugated to neuroactive drugs. A highly unsaturated fatty acid of twenty-two (22) carbon chain length is particularly preferred. Administration of the conjugate shows absorption into the brain. As is the case with adamantane conjugation, this approach requires metabolic transformation of the prodrug conjugate of enkephalin to restore the activity of the enkephalin peptide.

There is therefore a compelling need in the art for pharmaceutically acceptable and effective therapeutic/diagnostic compositions capable of traversing the BBB without substantial loss or diminution of their therapeutic or diagnostic character.

2. SUMMARY OF THE INVENTION

The present invention broadly relates to therapeutic and/or diagnostic drug oligomer conjugates wherein a drug molecule is covalently bonded to an oligomer to form an amphiphilic conjugate. In one aspect, the oligomer comprises at least one lipophilic moiety and at least one hydrophilic moiety, and the size and nature of the amphiphilic and lipophilic moieties is so selected as to impart an amphiphilic nature to the resulting conjugate.

The present invention relates generally to amphiphilic drug-oligomer conjugates capable of traversing the BBB and to methods of making and using such conjugates.

In one aspect, the therapeutics are neuroactive drugs, proteins, peptides, and especially enkephalin analogues. The conjugates are stable in the environment of the bloodstream and resist degradation by the enzymes of the BBB and in the CNS. Furthermore, the conjugates readily traverse the BBB.

In one aspect, the drug oligomer conjugates produce their intended pharmacological effect without undergoing metabolic cleavage of the oligomer.

In another aspect the lipophile and hydrophile are connected by a labile, hydrolyzable bond. When the bond is hydrolyzed in the CNS, the hydrophile remains attached to the drug.

The amphiphilic oligomers are composed of lipophilic and hydrophilic moieties. The lipophilic moieties are preferably natural fatty aids or alkyl chains. Preferably, the fatty-acid moiety is a straight chain molecule having (saturated or unsaturated) carbon atoms and suitably ranges from four (4) to twenty six (26) carbon atoms. Most preferably, the fatty acid has from fourteen (14) to twenty two (22) carbon atoms.

The hydrophilic moieties are preferably small segment of polyethylene glycol (PEG), preferably having 1–7 PEG units, and more preferably 1–5 PEG units. The length and composition of the lipophilic moieties and the hydrophilic moieties may be adjusted to obtain desired amphiphilicity.

In another aspect, a cholesterol or adamantane moiety is substituted for straight chain fatty acid portion of the oligomers.

Examples of preferred oligomers are as follows:

  (Formula 1);

wherein n=3 to 25 and m =1 to 7;

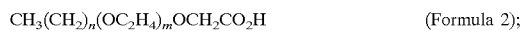  (Formula 2);

wherein n=3 to 25 and m=1 to 16;

  (Formula 3);

wherein n=3 to 25, m=1 to 7 and X=O;

  (Formula 4)

wherein m=0 to 5 and R=cholesterol or adamantane; or

  (Formula 5)

wherein m=0 to 5;

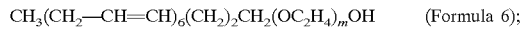  (Formula 6)

wherein m=0 to 7;

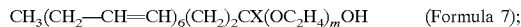  (Formula 7);

wherein m=1 to 7 and X=N or O.

Other unsaturated fatty acid moieties which can be used according to the present invention include oleic, linoleic, and linolenic.

For example, in one aspect, the lipophile and hydrophile are connected by hydrolyzable bonds. It is preferred to provide hydrolyzable bonds between the fatty acid and the hydrophilic moieties. This permits hydrolysis to occur after penetration into the CNS, thus releasing the active peptides with the hydrophilic group still attached to the peptide. As a result, the peptide acquires a more hydrophilic character and efflux to the circulatory system is thereby hindered.

Exemplary conjugates having non-hydrolyzable bonds are as follows:

(SEQ ID NO:1)

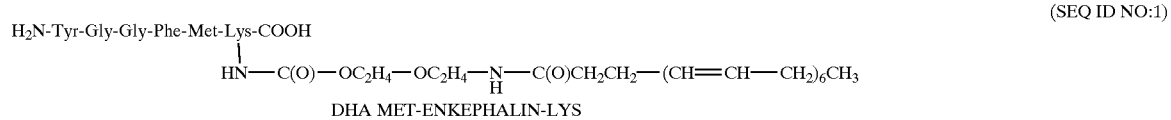

DHA MET-ENKEPHALIN-LYS (SEQ ID NO:1)

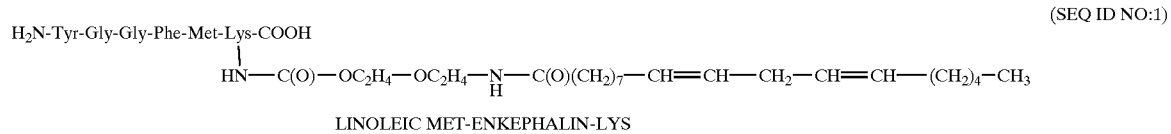

LINOLEIC MET-ENKEPHALIN-LYS

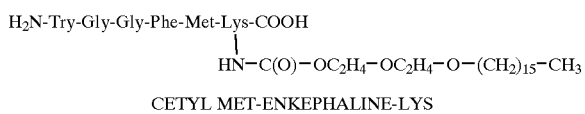

CETYL MET-ENKEPHALINE-LYS (SEQ ID NO:1)

In another aspect, the lipophile and hydrophile are connected by hydrolizable bonds.
For example:

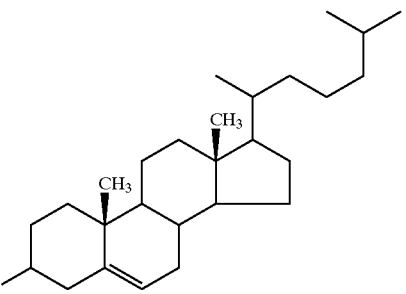

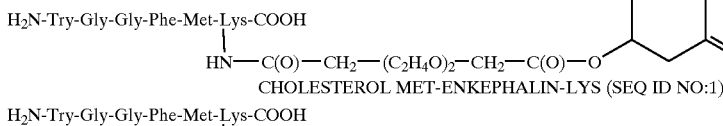

CHOLESTEROL MET-ENKEPHALIN-LYS (SEQ ID NO:1)

H$_2$N-Try-Gly-Gly-Phe-Met-Lys-COOH
  |
  HN—C(O)—O—(C$_2$H$_4$O)$_3$—C(O)—(CH$_2$)$_{14}$—CH$_3$

PALMITATE MET-ENKEPHALIN-LYS (SEQ ID NO:1)

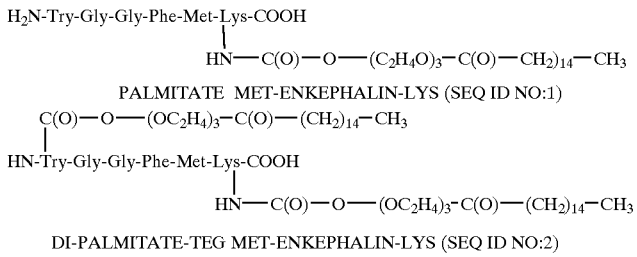

DI-PALMITATE-TEG MET-ENKEPHALIN-LYS (SEQ ID NO:2)

In one aspect, the covalent bond between the oligomer and the drug is preferably amide (a carboxy group of the oligomer is linked to an amine group of the peptide drug), or carbamate an chloroformate group of the oligomer is linked to an amine group of the peptide drug). In general, the derivitizable amine group of the peptide is the amine of the N-terminus or a nucleophilic amino residue, usually found on the epsilon amino residue of a lysine residue.

In another aspect, an ester (a carboxy group of the peptide is covalently coupled to a hydroxyl group of the oligomer or a carboxy group of the oligomer is covalently coupled to a hydroxyl group of the drug), amide (a carboxy group of the oligomer is linked to an amine group of the drug) or carbamate (an chloroformate group of the oligomer is linked to an amine group of the drug) bond is provided for non peptide drugs.

For the enkephalin analogues, the preferred peptides are leu enkephalin lysine (SEQ ID NO:50) and met enkephalin lysine (SEQ ID NO:49). The amino acid side chain of the lysine is preferably utilized in bonding.

The amphiphilic drug-oligomer conjugate may comprise multiple oligomers of differing compositions.

In another aspect, the amphiphilic drug oligomer conjugates moieties are configured as follows:
R—OCH$_2$CH$_2$OCH$_2$CH$_2$C(O)
OCH$_2$CH$_2$CH$_2$OCH$_2$CH$_2$CH$_2$NH-Enkephalin (SEQ ID NO:1); or
R—OCH$_2$CH$_2$OCH$_2$C(O)OCH$_2$CH$_2$NH-Enkephalin (SEQ ID NO:1).
Wherein R=alkyl$_{1-26}$, cholesterol or amantane.

Figure 1B:
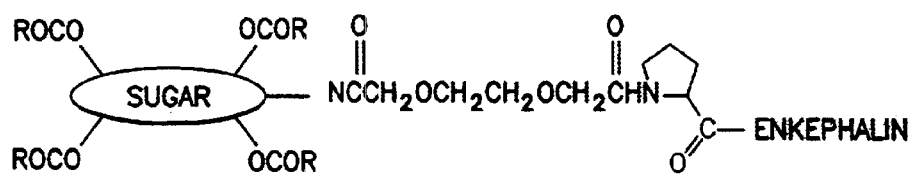
Figure 1C:
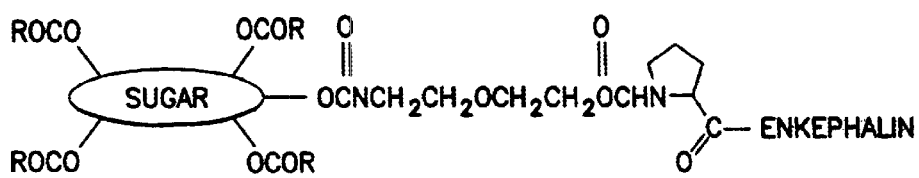

In another aspect of the amphiphilic oligomer moieties are sugar moieties coupled to natural fatty acids and segments of polyethylene glycol. The PEG moiety serves to increase the amphiphilicity of the fatty sugar. Examples of arrangements including sugar moieties are provided in FIGS. 1A–1C.

In another aspect, PEG is used as a spacer group in the amphiphilic conjugate and the length and number of the PEG moieties can be varied to refine the amphiphilicity of the conjugate. Increasing the number of PEGs increases the hydrophilicity of the conjugate.

In another aspect of the invention, a proline or alanine is added to the N-terminus of the peptide. In a preferred aspect, a proline or alanine is added to the N-terminus of an enkephalin peptide and the oligomer moiety is coupled to the N-terminus of the proline or alanine residue.

After absorption into the central nervous system, the esters of the fatty sugar are hydrolysized leaving a hydrophilic moiety. Efflux is hindered and the brain aminopeptidases cleave the proline or alanine portion leaving the peptide to regain full activity.

The invention also provides a pharmaceutical composition comprising an amphiphilic drug oligomer conjugate and a pharmaceutically acceptable carrier.

In another aspect, a pharmaceutical composition is provided comprising (1) a mixture of an enkephalin conjugate according to the present invention wherein the enkephalin peptide has proline or alanine added to its N-terminus and an enkephalin conjugate according to the present invention which does not have a proline or alanine added to the N-terminus, and (2) a pharmaceutical carrier. This aspect provides a faster acting sustained dose of enkephalin.

The invention also provides methods of administering a conjugate of the invention.

The invention further provides assays, both in vitro and in vivo, for testing the efficacy of the conjugates of the invention.

Other objects and further scope of applicability of the present invention will become apparent from the detailed description given hereafter. It should be understood that the detailed description and specific examples, while indicating preferred embodiments of the invention, are given byway of illustration only, since various changes and modifications will become apparent to those skilled in the art from the detailed description.

2.1 DEFINITIONS

As used herein, the term "lipophilic" means the ability to dissolve in lipids and/or the ability to penetrate, interact with and/or traverse biological membranes.

As used herein, the term, "lipophilic moiety" or "lipophile" means a moiety which is lipophilic and/or which, when attached to another chemical entity, increases the lipophilicity of such chemical entity, e.g., fatty acid, cholesterol.

As used herein, the term "hydrophilic" means the ability to dissolve in water.

As used herein, the term "hydrophilic moiety" or "hydrophile" refers to a moiety which is hydrophilic and/or which when attached to another chemical entity, increases the hydrophilicity of such chemical entity, e.g., sugars, PEG.

As used herein, the term "amphiphilic", means the ability to dissolve in both water and lipids.

As used herein, the term "amphiphilic moiety" means a moiety which is amphiphilic and/or which when attached to a peptide or non peptide drug increases the amphiphilicity of the resulting conjugate, e.g., PEG-fatty acid oligomer, sugar fatty acid oligomer.

As used herewith, the term "neuroactive drug" is used broadly to encompass any peptide or other drug having an activity within the CNS, e.g., enkephalin, enkephalin analogues.

As used herein the term "peptide" is intended to be broadly construed as inclusive of polypeptides per se having molecular weights of up to about 10,000, as well as proteins having molecular weights of greater than about 10,000.

As used herein, the term "covalently coupled" means that the specified moieties are either directly covalently bonded to one another, or else are indirectly covalently joined to one another through an intervening moiety or moieties, such as a bridge, spacer, or linkage moiety or moieties.

As used herein, the term "drug" means a substance intended for use in the diagnosis, characterization, cure, mitigation, treatment, prevention or allaying the onset of a disease, disease state, or other physiological condition or to enhance normal physiological functioning in humans and/or in non human animals.

For clarity of disclosure, and not by way of limitation, the detailed description of the invention is divided into the subsections which follow.

The present invention relates generally to amphiphilic drug oligomer conjugates capable of traversing the BBB and to methods of making and using such conjugates.

The drugs are preferably neuro-active drugs, proteins peptides and especially enkephalin analogues. The conjugates are stable in the environment of the bloodstream and resist degradation by the BBB. The conjugates readily traverse the BBB.

In one aspect, the conjugates produce their intended pharmacological effect without requiring metabolic cleavage of the oligomer. When cleavage of the oligomer occurs, the drug retains activity.

The amphiphilic oligomers are composed of lipophilic and hydrophilic moieties. The lipophilic moieties are preferably natural fatty acids or alkyl chains. The hydrophilic moieties are preferably small segments of PEG, having 1 to 7 PEG moieties, and preferably having 1 to 5 PEG moieties. The length and composition of the lipophilic moieties and the hydrophilic moieties may be adjusted to obtain desired amphiphilicity. For example, the carbon chains of the fatty acid or alkyl moieties may be lengthened to increase lipophilicity, while PEG moieties may be lengthened to increase hydrophilicity.

Preferably, the fatty acid moiety is a straight chain molecule having saturated and unsaturated carbons and ranges from four (4) to twenty-six (26) carbon atoms. Most preferably the fatty acid has from fourteen (14) to twenty two (22) carbon atoms.

A cholesterol or adamantane moiety can be substituted for straight chain fatty acid as the lipophilic portion of the oligomers.

Examples of preferred oligomers arenas follows:

$$CH_3(CH_2)_n(OC_2H_4)_mOH \qquad \text{(Formula 1)};$$

wherein n=3 to 25 and m=1 to 7;

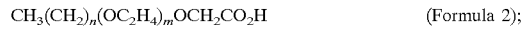
$$CH_3(CH_2)_n(OC_2H_4)_mOCH_2CO_2H \qquad \text{(Formula 2)};$$

wherein n=3 to 25 and m=1 to 6;

$$CH_3(CH_2)_nCO(OC_2H_4)_mOH \qquad \text{(Formula 3)};$$

wherein n=3 to 25, and m=1 to 7;

$$R-(OC_2H_4)_mCH_2CO_2H \qquad \text{(Formula 4)}$$

wherein m=0 to 5 and R=cholesterol or adamantane; or

$$R-OCO(C_2H_4O)_mCH_2CO_2H \qquad \text{(Formula 5)};$$

wherein m=0 to 5,

$$CH_3(CH_2H-CH=CH)_6(CH_2)_2CH_2(OC_2H_4)_mOH \qquad \text{(Formula 6)};$$

wherein m=1 to 7;

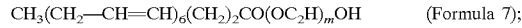
$$CH_3(CH_2-CH=CH)_6(CH_2)_2CO(OC_2H)_mOH \qquad \text{(Formula 7)};$$

wherein m=1 to 7.

Other unsaturated fatty acid moieties which can be used according to the present invention include oleic, linoleic and linolenic.

In certain instances, it is preferred to provide hydrolyzable bonds between the polyethylene glycol and the fatty acid moieties. This permits hydrolysis to occur after penetration into the central nervous system thus releasing the active peptides with the polyethylene glycol group still attached to the peptide. The peptides acquire a more hydrophilic character and efflux to circulatory system is thereby hindered.

3. BRIEF DESCRIPTION OF THE FIGURES 3.1 FIGS. 1A–1C: Formulae 8–10 amphiphilic oligomers of the present invention where in the lipophile is a sugar. In 1b and 1c, PEG is used as a spacer group. In 1A–1C a proline residue is added at the N-terminus of the enkephalin peptide.

Figure 2:
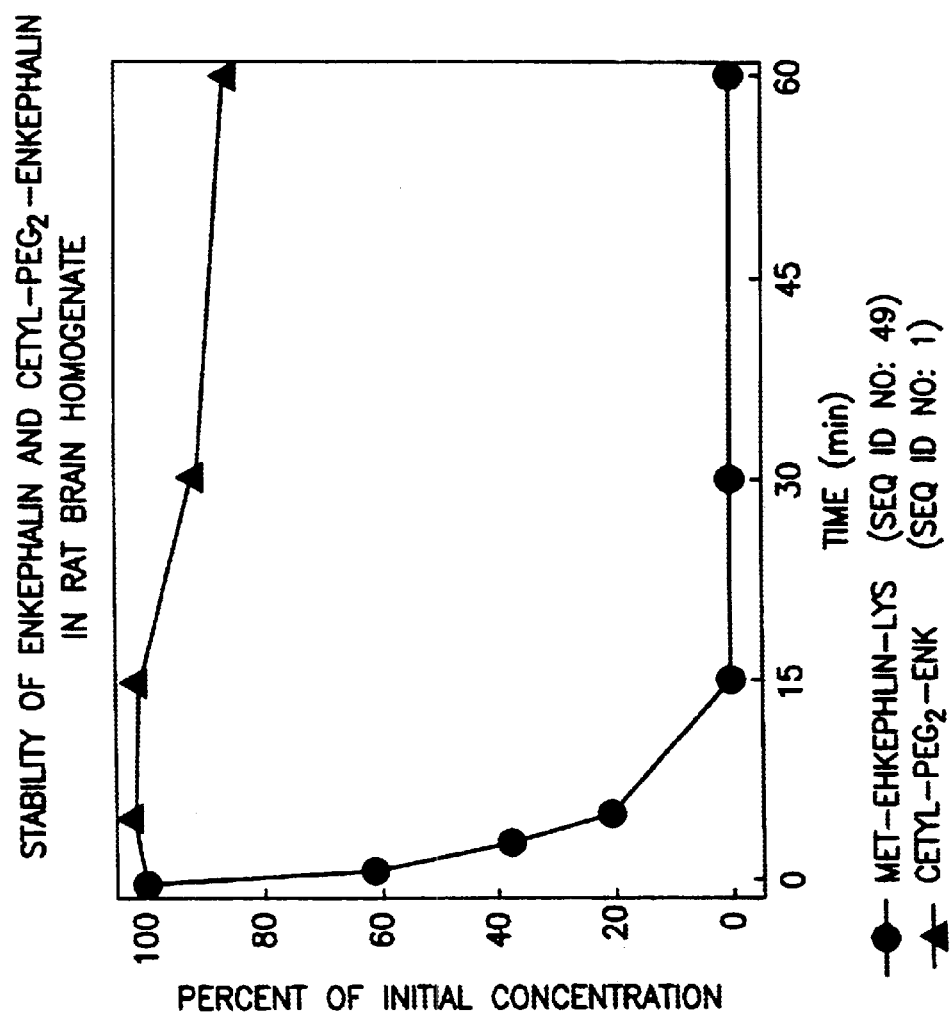

3.2 FIG. 2: Compares the stability of the cetyl-PEG2enkephalin-lys (SEQ ID NO:1) conjugate (non hydrolyzable) to unconjugated enkephalin (SEQ ID NO:48) in rat brain homogenate.

Figure 3:
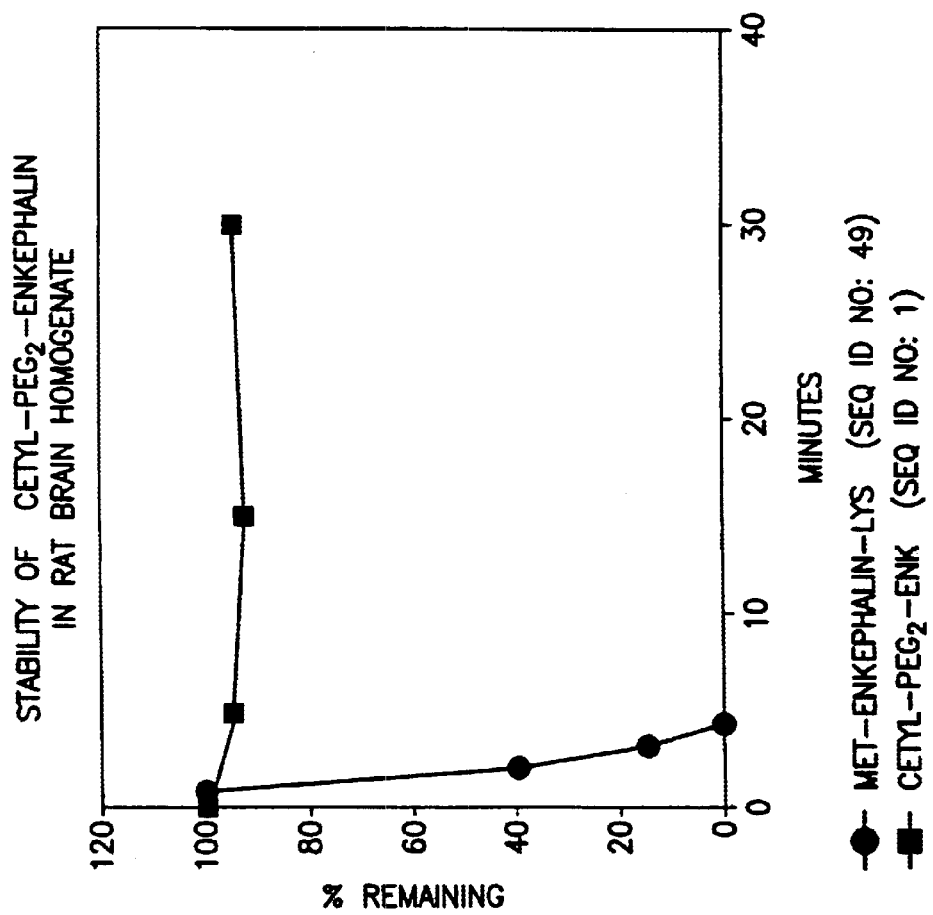

3.3 FIG. 3: Compares the stability of the cetyl-PEG3enkephalin (SEQ ID NO:1) conjugate (non-hydrolyzable) to unconjugated enkephalin (SEQ ID NO:47) in rat brain homogenate.

Figure 4:
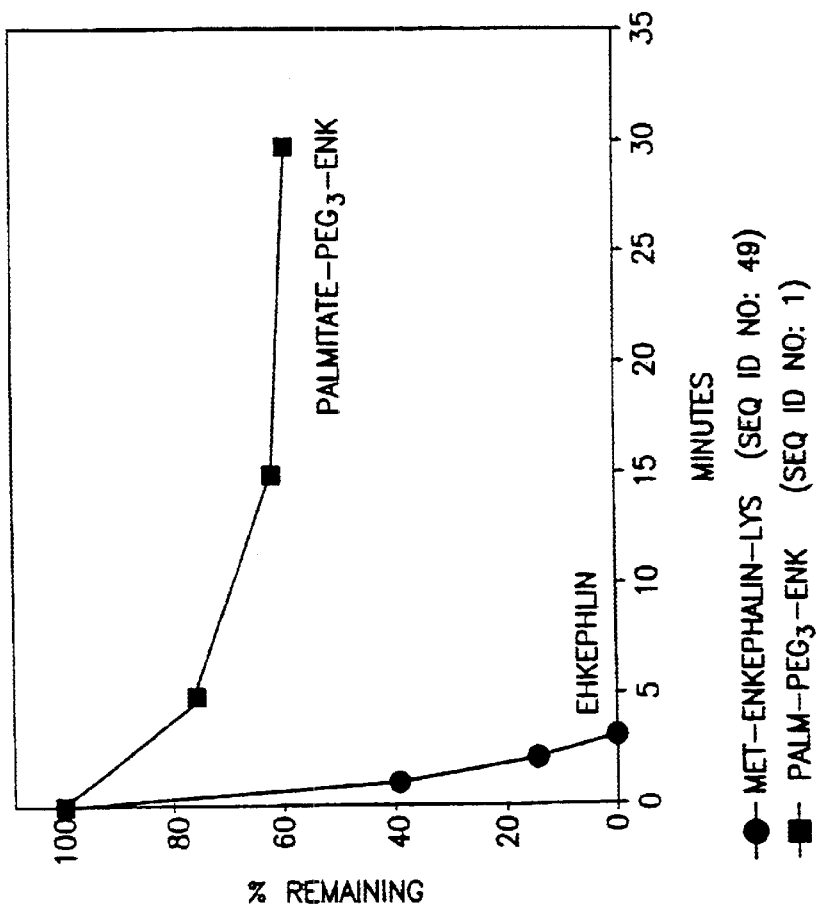

3.4 FIG. 4: Compares palmitate-PEG3-Enk (SEQ ID NO:1) conjugate (hydrolyzable) to unconjugated enkephalin (SEQ ID NO:47) in rat brain homogenate.

3.5 FIG. 5a–5d: HPLC data showing extraction of conjugate from homogenized rat brain.

Figure 6:
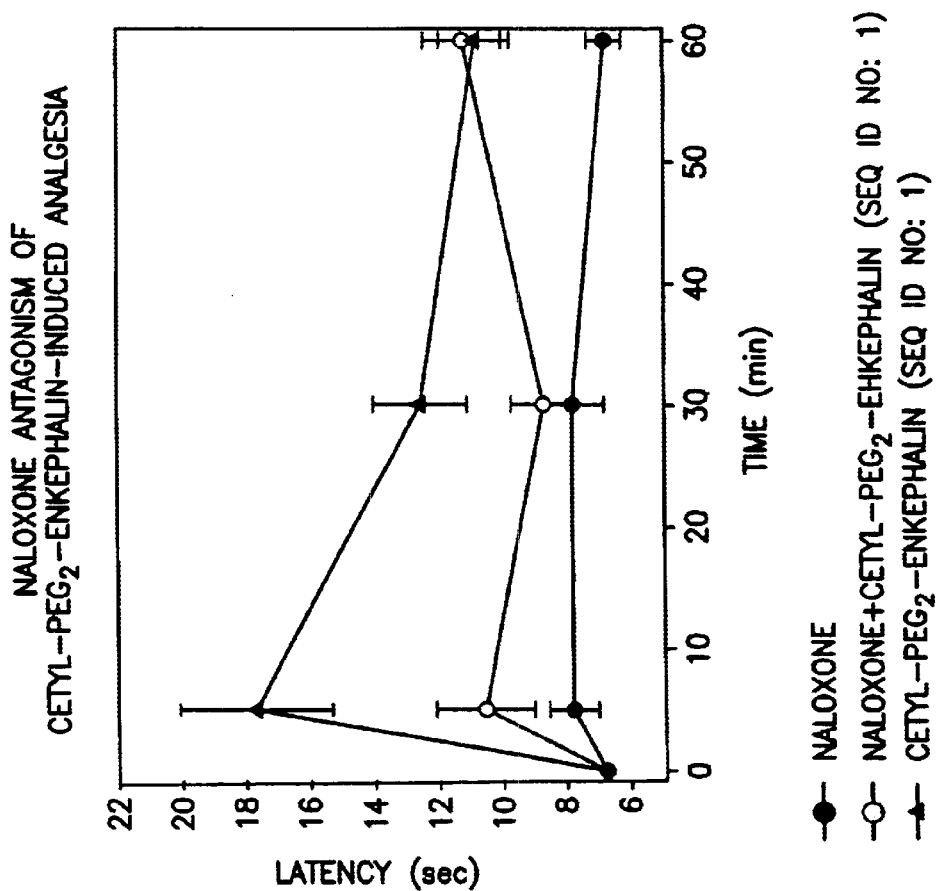

3.6 FIG. 6: Graph demonstrating competitive binding between cetyl-PEG$_2$enkephalin (SEQ ID NO:1) conjugate and naloxone, an Opioid μ receptor agonist.

Figure 7:
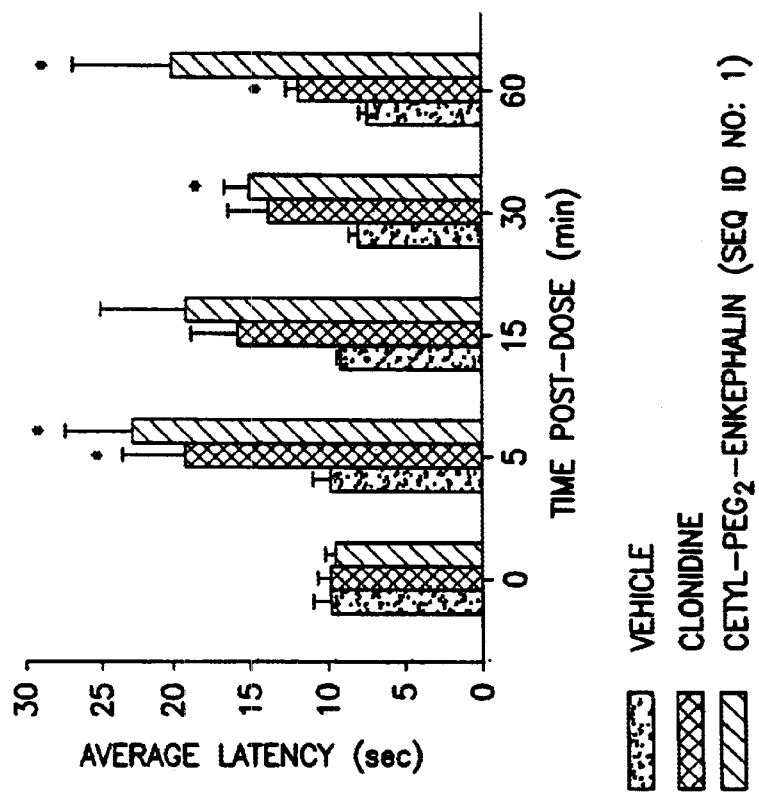

3.7 FIG. 7: Graphic comparison of analgesic effect of cetyl-PEG$_2$enkephalin (SEQ ID NO:1) with clonidine (a morphine substitute).

3:8 FIG. 8: Table showing results of receptor binding assays for various conjugates according to the present invention.

Figure 9:
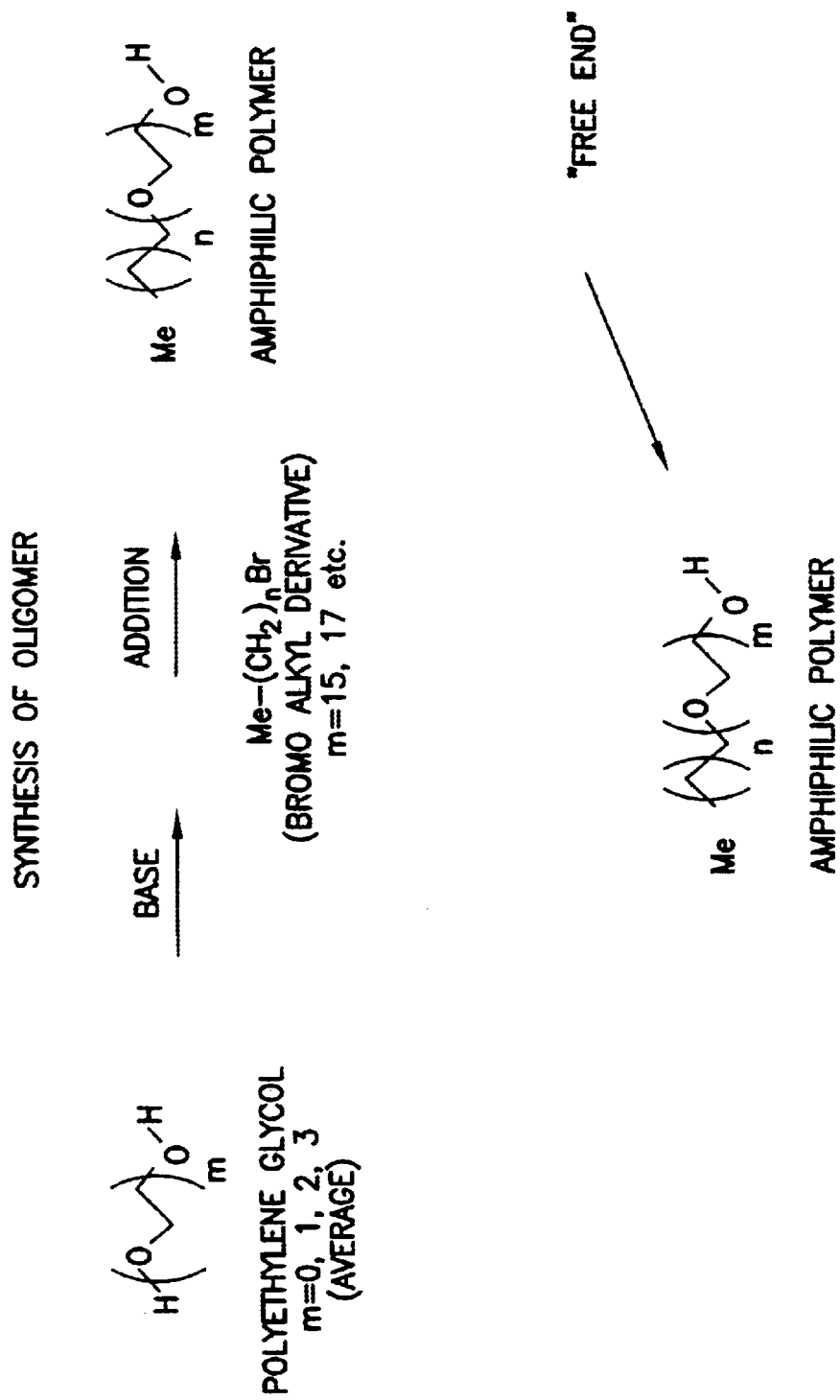

3.9 FIG. 9: Exemplary synthetic scheme for an oligomer according to the present invention.

3.10 FIG. 10: Exemplary synthetic scheme showing attachment of an oligomer to an enkephalin peptide according to the present invention.

4. DETAILED DESCRIPTION OF THE INVENTION

The covalent bond between the oligomer and the drug is preferably amide (a carboxy group of the oligomer is linked to an amine group of the peptide), or carbamate (a chloroformate Aid , group of the oligomer is linked to an amine group of the peptide).

For non peptide drug, the bond is preferably ester (a carboxy group of the drug is covalently coupled to a hydroxyl group of the oligomer or a carboxy group of the oligomer is covalently coupled to a hydroxyl group of the drug), amide (a carboxy group of the oligomer is linked to an amine group of the drug) or carbamate (a chloroformate group of the oligomer is linked to an amine group of the drug). For the enkephalin analogues, the preferred peptides are leu-enkephalin lysine (SEQ ID NO:50) and met enkephalin lysine (SEQ ID NO:49). The amino residue of the lysine is preferably utilized in bonding.

Other preferred amphiphilic moieties are sugar moieties, coupled to natural fatty acids and segments of polyethylene glycol. The PEG moiety serves to increase the amphiphilicity of the fatty sugar.

The length and number of the PEG moieties can be varied to refine the amphiphilicity of the conjugate. Increasing the number of PEGs increases the hydrophilicity of the resulting oligomer.

In certain instances, it is preferred to modify the N-terminus of an enkephalin with proline or alanine before attaching the oligomer. After absorption into the central nervous system, the esters of the fatty sugar are hydrolysized leaving hydrophilic moiety. Easy efflux is hindered and the brain aminopeptidases cleave the proline or alanine portion leaving the peptide to regain full activity.

Where the hydrophilic moiety is a sugar, it is preferred that the sugar is a monosaccharide. The sugar may be an amino sugar or a non amino sugar.

In another aspect, the oligomer is attached to the C-terminus of the peptide drug. For example:
R—OCH$_2$CH$_2$OCH$_2$C(O)OCH$_2$CH$_2$CH$_2$OCH$_2$CH$_2$CH$_2$NH-Enkephalin (SEQ ID NO:1); or
R—OCH$_2$CH$_2$OCH$_2$C(O)OCH$_2$CH$_2$NH-Enkephalin (SEQ ID NO:1).

Wherein R=alkyl$_{1-26}$, cholesterol or amantane.

In another aspect, the oligomer is attached at the N-terminus of the peptide drug. For example:

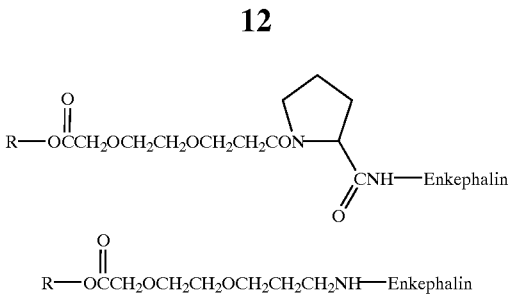

It will be appreciated by one of skill in the art that the oligomers may be attached at the carboxy terminus or at a constituent of an amino acid side chain, such as a the amino group of lystine.

The present invention broadly relates to therapeutic and/or diagnostic conjugates wherein the therapeutic and/or diagnostic molecule is covalently bonded to an oligomer to form an amphiphilic conjugate. In one aspect, the oligomer comprises at least one lipophilic moiety and at least one hydrophilic moiety, and the size and nature of the two moieties is so selected as to impart an amphiphilic nature to the resulting conjugate.

Exemplary oligomers according to the present invention are as follows:

$CH_3(CH_2CH=CH)6(CH_2)_2CH_2(OC_2H_4)_mOH$,
where m=1 to 7;
$CH_3(CH_2CH=CH)_6(CH_2)_2CO(OC_2H_4)_mOH$,
where m=1 to 7;
$CH_3(CH_2CH=CH)_6(CH_2)_2CONHCH_2CH_2(OC_2H_4)_mOH$,
where m=1 to 6;
$CH_3(CH_2CH=CH)_6(CH_2)_3(OC_2H_4)_mOCH_2COOH$,
where m=1 to 6;
$CH_3(CH_2CH=CH)_6(CH_2)_2CO(OC_2H4)_mOCH_2COOH$,
where m=1 to 6;
$CH_3(CH_2)_7CH=CH(CH_2)_8(OC_2H_4)_mOH$,
where m=1 to 7;
$CH_3(CH_2)_7CH=CH(CH_2)_7CO(OC_2H_4)_mOH$,
where m=1 to 7;
$CH_3(CH_2)_7CH=CH(CH_2)_7CONHCH_2CH_2(OC_2H_4)_mOH$,
where m=1 to 6;
$CH_3(CH_2)_7CH=CH(CH_2)_8(OC_2H_4)_mOCH_2COOH$,
where m=1 to 6;
$CH_3(CH_2)_7CH=CH(CH_2)_7CO(OC_2H_4)_mOCH_2CH_2OH$,
where m=1 to 6;
$CH_3(CH_2)_4CH=CHCH_2CH=CH(CH_2)_7CH_2(OC_2H_4)_mOH$,
where m=1 to 6;
$CH_3(CH_2)_4CH=CHCH_2CH=CH(CH_2)_7CO(OC_2H_4)_mOH$,
where m=1 to 7;
$CH_3(CH_2)_4CH=CHCH_2CH=CH(CH_2)_7CONHCH_2CH_2(OC_2H_4)_mOH$,
where m=1 to 6;
$CH_3(CH_2)_4CH=CHCH_2CH=CH(CH_2)_7CO(OC_2H_4)_mOCH_2COOH$,
where m=1 to 6;
$CH_3(CH_2)_4CH=CHCH_2CH=CH(CH_2)_7CH_2(OC_2H_4)_mOCH_2COOH$,
where m=1 to 6;
$CH_3(CH_2CH=CH)_3(CH_2)_7CH_2(OC_2H_4)_mOH$
where m=1 to 7;

$CH_3(CH_2CH=CH)_3(CH_2)_7CO(OC_2H_4)_mOH$,
where m=1 to 7;
$CH_3(CH_2CH=CH)_3(CH_2)_7CONHCH_2CH_2(OC_2H_4)_mOH$,
where m=1 to 6;
$CH_3(CH_2CH=CH=CH_3(CH_2)_7CO(OC_2H_4)_mOCH_2COOH$,
where m=1 to 6;
$CH_3(CH_2CH=CH=CH_3(CH_2)_7CH_2(OC_2H_4)_mOCH_2COOH$,
where m=1 to 6.

4.1 Therapeutic Compounds

The invention thus comprehends various compositions for therapeutic (in vivo) application, wherein the peptide component of the conjugated peptide complex is a physiologically active, or bioactive, peptide. In such peptide containing compositions, the conjugation of the peptide component to the oligomer may be by direct covalent bonding or indirect (through appropriate spacer groups) bonding, and the hydrophilic and lipophilic moieties may also be structurally arranged in the oligomer in any suitable manner involving direct or indirect covalent bonding, relative to one another. A wide variety of peptide species may be accommodated in the broad practice of the present invention, as necessary or desirable in a given end use therapeutic application.

While the description is primarily and illustratively directed to the use of enkephalin as a peptide component in various compositions and formulations of the invention, it will be appreciated that the utility of the invention is not thus limited, but rather extends to any peptide species which is capable of conjugation to the oligomers herein described, or which is capable of being modified, as for example by the incorporation of a proline residue, so as to enable the peptide to be conjugated to the oligomers described herein.

Accordingly, appropriate peptides include, but or not limited to: adrenocorticotropic hormone, adenosine deaminase ribonuclease, alkaline phosphatase, angiotensin, antibodies, arginase, arginine deaminease, asparaginase, caerulein, calcitonin, chemotrypsin, cholecystokinin, clotting factors, dynorphins, endorphins, endorphins, enkephalins, enkephalins, erythropoietin, gastrin releasing peptide, glucagon, hemoglobin, hypothalmic releasing factors, interferon, katacalcin, motilin, neuropeptide Y, neurotensin, non-naturally occurring opioids, oxytosin, papain, parathyroid hormone, peptides prolactin, soluble CD-4, somatomedin, somatostatin, somatostatin, somatotropin, superoxide dismutase, thyroid stimulating hormone, tissue plasminogen activator, trypsin, vasopressin, and analogues of such peptides, as well as other suitable enzymes, hormones, proteins, polypeptides, enzyme protein conjugates, antibody-hapten conjugates, viral epitopes, etc.

In another aspect, the therapeutic peptide of the amphiphilic drug oligomer conjugates are as described in U.S. Pat. No. 5,641,861, which is incorporated herein by reference, so long as any of such peptides contains a lysine residue. Exemplary peptides described therein include: Ac-Phe-Arg-Trp-Trp-Tyr-Lys—NH$_2$ (SEQ ID NO:4); Ac-Arg-Trp-Ile-Gly-Trp-Lys-NH2 (SEQ ID NO:5); Trp-Trp-Pro-Lys-His-Xaa—NH2 (SEQ ID NO:6), where Xaa can be any one of the twenty naturally occurring amino acids, or Trp-Trp-Pro-Xaa—NH$_2$ (SEQ ID NO:7), where Xaa is Lys or Arg; Tyr-Pro-Phe-Gly-Phe-Xaa—NH$_2$ (SEQ ID NO:8), wherein Xaa can be any one of the twenty naturally occurring amino acids; (D)Ile-(D)Met-(D)Ser-(D)Trp-(D)Trp-Gly$_n$-Xaa—NH2 (SEQ ID NO:9), wherein Xaa is Gly or the D-form of a naturally occurring amino acid and n is 0 or 1, peptides of this formula can be hexapeptides when Gly is absent (n is 0) and heptapeptides when Gly is present (n is 1); (D)Ile-(D)Met-(D)Thr-(D)Trp-Gly-Xaa—NH$_2$ (SEQ ID NO:10), wherein Xaa is Gly or the D-form of a naturally occurring amino acid; Tyr-Al-B2-C3—NH$_2$ (SEQ ID NO:11), wherein Al is (D)Nve or (D)Nle, B2 is Gly, Phe, or Trp, and C3 is Trp or Nap; Pm and red {Me$_x$H$_y$N-Tyr-(NMe)$_z$-Tyr-Xaa$_z$—NH$_2$} (SEQ ID NO:12), wherein x and y independently are 0,1, or 2and z is 0 or 1, D4 is Lys or Arg and Xaa is Phe, D-Phe, or NHBzl; Trp-Trp-Pro-D4-His$_z$-Xaa$_2$ (SEQ ID NO:13), wherein z is 0 or 1, D4 is Lys or Arg and Xaa is any one of the naturally-occurring amino acids.

In still another aspect, the therapeutic peptide of the amphiphilic drug oligomer conjugates are as described in U.S. Pat. No. 5,602,099, which is incorporated herein by reference with the proviso that the conjugation can occur only where there is a free carboxyl or free N-terminal. Exemplary peptides include: H-Tyr-Tic-Phe-Phe-OH (SEQ ID NO:14); H-Tyr-Tic-Phe-Phe-NH$_2$ (SEQ ID NO:15); Tyr(NαMe)-Tic-Phe-Phe-OH (SEQ ID NO:16); Tyr(NαCpm)-Tic-Phe-Phe-OH (SEQ ID NO:17); Tyr(NαHex)-Tic-Phe-Phe-OH (SEQ ID NO:18); Tyr(NαEt$_2$)-Tic-Phe-Phe-OH (SEQ ID NO:19); H-Dmt-Tic-Phe-Phe-OH (SEQ ID NO:20); H-Dmt-Tic-Phe-Phe-NH$_2$(SEQ ID NO:21); H-Tyr(3-F)-Tic-Phe-Phe-OH (SEQ ID NO:22); H-Tyr(3-Cl)-Tic-Phe-Phe-OH (SEQ ID NO 23); H-Tyr(3-Br)-Tic-Phe-Phe-OH (SEQ ID NO:24); H-Dmt-TicΨT[CH$_2$—NH]Phe-Phe-OH (SEQ ID NO:25); H-Dmt-TicΨ[CH$_2$-NH]Phe-Phe-NH$_2$ (SEQ ID NO:26); H-Tyr-TicΨ[CH$_2$—NCH$_3$]Phe-Phe-OH (SEQ ID NO:27); H-Tyr-TicΨ[CH$_2$—NH]Hfe-Phe-OH (SEQ ID NO:28); Tyr(NMe)-TicΨ[CH$_2$—NH]Hfe-Phe-OH [)] (SEQ ID NO:29); H-Tyr-Tic-Phg-Phe-OH (SEQ ID NO:30); H-Tyr-Tic-Trp-Phe-OH (SEQ ID NO:31); H-Tyr-Tic-Trp-Phe-NH$_2$(SEQ ID NO:32); H-Tyr-Tic-His-Phe-OH (SEQ ID NO:33); H-Tyr-Tic-2-Nal-Phe-OH (SEQ ID NO:34); H-Tyr-Tic-Atc-Phe-OH (SEQ ID NO:35); H-Tyr-Tic-Phe-Phe(pNO$_2$)-OH (SEQ ID NO:36); H-Tyr-Tic-Trp-Phe(pNO$_2$)-OH (SEQ ID NO:37); H-Tyr-Tic-Phe-Trp-NH$_2$ (SEQ ID NO:38); H-Tyr-Tic-Phe-Phe-Val-Val-Gly-NH$_2$ (SEQ ID NO:39); H-Tyr-Tic-Phe-Phe-Tyr-Pro-Ser-NH$_2$ (SEQ ID NO:40); H-Tyr-Tic-Trp-Phe-Tyr-Pro-Ser-NH$_2$ (SEQ ID NO:41); H-Tyr-Tic-Trp-Phe (pNO$_2$)-Tyr-Pro-Ser-NH$_2$ (SEQ ID NO:42) and H-Tyr-Tic-Phe-Phe-Leu-Nle-Asp-NH2 (SEQ ID NO:43).

Abbreviations in the aforementioned peptides of U.S. Pat. No. 5,602,099 may be interpreted as follows: Aib=α-aminoisobutyric acid; Atc=2-aminotetralin-2carboxylic acid; Boc=tert-butoxycarbonyl; Cpm=cyclopropylmethyl; DCC=dicyclohexyl carbodiimide; D1EA=diisopropylethylamine; Dmt=2,6-dimethyltyrosine; Et=ethyl; Hex=hexyl; Hfe=homophenylalanine; HOBt=1-hydroxybenzotriazole; MVD=mouse vas deferens; 1-Nal=3-(1'-naphthyl)alanine; 2-Nal=3-(2'-naphthyl)alanine; Phe(pNO$_2$)=4-nitrophenylalanine; Phg=phenylglycine; Tic=1,2,3,4-tetrahydroisoquinoline-3carboxylic acid; TIP=H-Tyr-Tic-Phe-OH (SEQ ID NO:44); TIP-NH$_2$=H-Tyr-Tic-Phe-NH$_2$ (SEQ ID NO:45); TIP(Ψ)=H-Tyr-TicΨ[CH$_2$—NH]Phe-OH (SEQ ID NO:46); TIPP=H-Tyr-Tic-Phe-Phe-OH (SEQ ID NO:14); TIPP-NH$_2$=H-Tyr-Tic-Phe-Phe-NH$_2$ (SEQ ID NO:15); TIPP(Ψ)=H-Tyr-TicΨ[CH$_2$-NH]Phe-Phe-OH (SEQ ID NO:47); Tyr(3-Br)=3-bromotyrosine; Tyr(3-Cl)=3chlorotyrosine; Tyr(3-F)=3-fluorotyrosine; and Tyr (NαMe)=Nα-methyltyrosine.

In another aspect, the peptides are as described in U.S. Pat. No. 5,545,719, which is incorporated herein by reference.

Other exemplary peptides include, for example, ACTH-related peptides for inducing neural regeneration, cyclosporin for treating infection, enkephalin analogs for treating pain and drug addiction, MIF-1 for treating depression, neurotensin for relieving pain, and peptide T for treating AIDS-associated dementia. Adrenocorticotropic hormone (ACTH) and its analogue peptides are also known to restore the avoidance learning caused by removal of the pituitary gland and can also be used to treat passive avoidance conditions.

Particularly preferred peptides are endogenous and synthetic Opioid peptides such as the enkephalins. A particularly preferred Opioid is [Met$^5$]Enkephalin (Tyr-Gly-Gly-Phe-Met) (SEQ ID NO:48).

Peptides according to the present invention may be synthesized according to any method of synthesis known in the art. Such methods include, but are not limited to chemical synthesis techniques and recombinant DNA expression techniques.

The therapeutic compounds of the present invention can be modified in order to facilitate coupling to the amphiphilic oligomer. A functional group may be added to the C-terminus or the N-terminus of the peptide or to a side chain of the peptide in order to provide a point of attachment for the oligomer.

Alternatively, specific amino acids may be inserted within the amino acid chain of the peptide therapeutic, or may replace an amino acid of the therapeutic or may be added to the C-terminus or N-terminus of the peptide in order to facilitate attachment of the oligomer where such modification does not eliminate the activity of the peptide. For example, a proline or alanine residue can be added to the N-terminus of a therapeutic peptide, such as an enkephalin, such as [met$^5$]enkephalin, in order to facilitate attachment of the amphiphilic oligomer.

One skilled in the art would know that one or more amino acids within the exemplified. peptides could be modified or substituted, as for example, by a conservative amino acid substitution of one or more of the specific amino acids shown in the exemplified peptides. A conservative amino acid substitution change can include, for example, the substitution of one acidic amino acid for another acidic amino acid, of one hydrophobic amino acid for another hydrophobic amino acid or other conservative substitutions known in the art, including the use of non naturally occurring amino acids, such as Nle for Leu or ornithine (Orn) or homoArginine (homoArg) for Arg.

In addition to the above types of modifications or substitutions, a mimic of one or more amino acids, otherwise known as a peptide mimetic or peptidomimetic, can also be used. As used herein, the term "mimic" means an amino acid or an amino acid analog that has the same or similar functional characteristics of an amino acid. Thus, for example, a (D)arginine analog can be a mimic of (D)arginine if the analog contains a side chain having a positive charge at physiological pH, as is characteristic of the guanidinium side chain reactive group of arginine. A peptide mimetic or peptidomimetic is and organic molecule that retains similar peptide chain pharmacophore groups as are present in the correspinding pertide.

The substitution of amino acids by non-naturally occurring amino acids and peptidomimetics as described above can enhance the overall activity or properites of an individual peptide based on the modifications to the side chain functionalities. For example, these types of alterations can be employed along with the amphiphilic oligomers of the present invention to further enhance the peptide's stability to enzymatic breakdown and increase the peptide's biological activity.

One skilled in the art can easily synthesize the peptides for use as therapeutics in this invention. Standard procedures for preparing synthetic peptides are well known in the art. The peptides can be synthesized using the solid phase peptide synthesis (SPPS) method of Merrifield (*J. Am. Chem. Soc.*, 85:2149 (1964), which is incorporated herein by reference) or using standard solution methods well known in the art (see, for example, Bodanzsky, M., *Principles of Peptide Synthesis* 2nd revised ed. (Springer-Verlag, 1988 and 1993), which is incorporated herein by reference). Alternatively, simultaneous multiple peptide synthesis (SMPS) techniques well known in the art can be used. Peptides prepared by the method of Merrifield can be synthesized using an automated peptide synthesizer such as the Applied Biosystems 431A-01 Peptide Synthesizer (Mountain View, Calif.) or using the manual peptide synthesis technique described by Houghten, *Proc. Natl. Acad. Sci., USA* 82:51.31 (1985), which is incorporated herein by reference.

Peptides can be synthesized using amino acids or amino acid analogs, the active groups of which are protected as necessary using, for example, a t-butyldicarbonate (t-BOC) group or a fluorenylmethoxy carbonyl (FMOC) group. Amino acids and amino acid analogs can be purchased commercially (Sigma Chemical Co.; Advanced Chemtec) or synthesized using methods known in the art. Peptides synthesized using the solid phase method can be attached to resins including 4-methylbenzhydrylamine (MBHA), 4-(oxymethyl)-phenylacetamidomethyl and 4-(hydroxymethyl)phenoxymethylcopoly(styrene-1% divinylbenzene) (Wang resin), all of which are commercially available, or to p-nitrobenzophenone oxime polymer (oxime resin), which can be synthesized as described by De Grado and Kaiser, *J. Org. Chem.* 47:3258 (1982), which is incorporated herein by reference.

A newly synthesized peptide can be purified using a method such as reverse phase high performance liquid chromatography (RP-HPLC) or other method s of separation based on the size or charge of the peptide. ° Furthermore, the purified peptide can be characterized using these and other well known methods such as amino acid analysis and mass spectrometry.

4.2 SYNTHESIS

A general synthesis scheme for the oligomers of the present invention is provided in FIG. 9, and a general synthesis scheme for attaching such oligomer to the therapeutic peptides of the instant invention is provided in FIG. 10.

Several methods of modifying fatty acid to achieve the desired oligomer will be discussed in further detail with structural illustrations.

In the synthesis of oligomers containing fatty acids and polyethylene glycols, where the ethylene glycol is connected to the fatty acid in a hydrolysable ester bond, it is desirable to start with the acid chloride of the fatty acid or its acid anhydride. A desired polyethylene glycol having two free hydroxyls at the termini is then treated in inert solvent with equal molar equivalent of acid chloride or acid anhydride. The glycol unit is first dissolved in inert solvent and treated with organic base before the addition of the acid chloride or acid anhydride. The product is extracted from the reaction medium and further purified using column chromatograph:

-continued
$$CH_3(CH_2)_nCO(OC_2H_4)_mOH$$

In some instances it is desired to create oligomers that have stronger hydrolysable bond such as amide. The acid chloride or the acid anhydride of the selected fatty acid is treated with amino derivative of polyethylene glycol in a controlled reaction condition to effect only the amino residue and not the hydroxyl portion. Other conditions that ensure selectivity is by converting the fatty acid into N-hydroxysuccinimide ester and reacting with the amino residue of the polyethylene glycol.

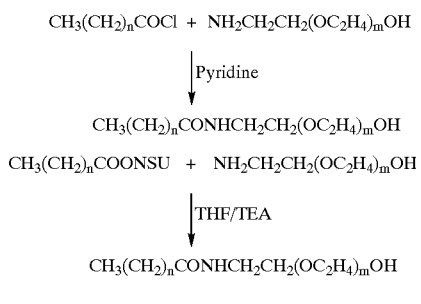

Coupling of the oligomer to the peptide drug is effected by converting the free hydroxyl moiety of the oligomer to N-hydroxysuccinimide ester (NSU). N-hydroxysuccinimide group reacts readily with the nucleophilic amino residue of the peptide.

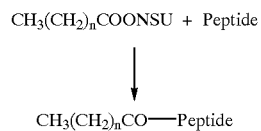

In the synthesis of oligomers in which the lipophilic portion of the oligomers is connected to the hydrophilic portion by ether linkage, the desired polyethylene glycol (hydrophile) is first protected. One of the two free hydroxyls at the termini is protected with a trityl group in pyridine using one mole of trityl chloride. The protected polyethylene glycol is dissolved in a suitable inert solvent and treated with sodium hydride. Bromo or tosylate derivative of the lipophilic portion is dissolved in inert solvent and added to the solution of the protected polyethylene glycol. The product is treated with a solution of para-toluenesulfonic acid in anhydrous inert solvent at room temperature. The desired product is extracted in inert solvent and purified by column chromatography. The structures of the transformation are depicted below:

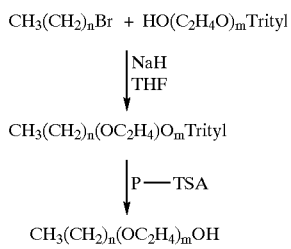

The lipophilic portion can be alkyl, cholesteryl, adamantyl moieties.

In the synthesis of oligomers where the lipophilic portion of the oligomer is connected to the hydrophilic portion in ether bond and the terminal ends in carboxylic acid moiety, it is desirable to protect the carboxylic group. Polyethylene glycol having free hydroxyl group at one end and carboxylic group at the other end is selected. The carboxylic group is protected by esterification. The protected polyethylene glycol is dissolved in a suitable inert solvent and treated with sodium hydride. Bromo or tosylate derivatives of the lipophilic portion is dissolved in inert solvent and added to the solution of the protected polyethylene glycol. The product is treated with solution of sodium hydroxide to liberate free acid. The desired product is extracted in inert solvent and purified by column chromatography. The structures of the transformation are depicted below.

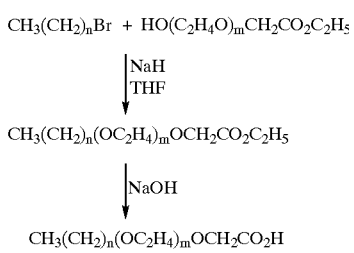

The lipophilic portion can be alkyl, cholesteryl or adamantyl moieties.

This group of acidic oligomers can be coupled to peptide drugs by first reacting the carboxylic group with N-hydroxysuccinimide (NSU) to from easily leavable group. A solution of the activated oligomers in inert solvent is treated with the desired peptide drug dissolved in a suitable solvent. Inverse addition may be selected.

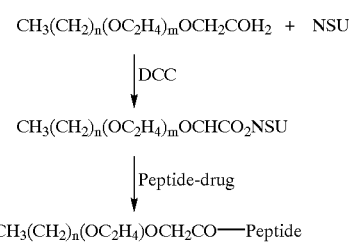

Sometimes it is desirable to replace the lipophilic moiety with lipophilic sugars. The sugar moiety is first esterified with desired fatty acid chloride to obtain selective or partial acylation. The product is treated in inert solvent with diacid chloride of desired dicarboxylic acid derivative of polyethylene glycol.

Reaction is conducted with one molar equivalent of each reacting moiety. This reaction leaves one end of the hydrophile bearing acid chloride, which is further converted to N-hydroxysuccinimide ester. The activated ester is reacted with peptide drug in suitable inert solvent.

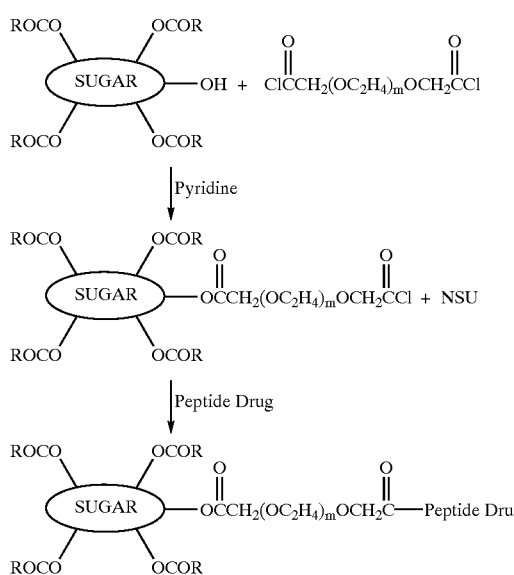

Where R=fatty acid, alkyll$_{1-26}$, cholesterol or adamantane.

4.3 Therapeutic Methods

The invention provides methods of treatment and prevention by administration to a subject of an effective amount of an amphiphilic drug oligomer conjugate of the invention.

One embodiment of the invention provides for methods of administering a pharmaceutical composition which is comprised of a therapeutically effective amount of an amphiphilic drug oligomer conjugate according to the present invention.

Methods of introduction include but are not limited to intradermal, intramuscular, intraperitoneal, intravenous, subcutaneous, intranasal, epidural, and oral routes. The conjugates may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

In certain circumstances, it may be desirable to introduce the pharmaceutical compositions of the invention directly into the central nervous system by any suitable route, including intraventricular and intrathecal injection; intraventricular injection may be facilitated by an intraventricular catheter, for example, attached to a reservoir, such as an Ommaya reservoir.

Pulmonary or nasal administration can also be employed, e.g., by use of an inhaler or nebulizer, and formulation with an aerosolizing agent.

In another embodiment, the conjugates can be delivered in a controlled release system. In one embodiment, a pump may be used (see Langer, supra; Sefton, *CRC Crit. Ref. Biomed. Eng.* 14:201 (1987); Buchwald et al., *Surgery* 88:507 (1980); Saudek et al., *N. Engl. J. Med.* 321:574 (1989)). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115–138 (1984)).

Other controlled release systems are discussed in the review by Langer (*Science* 25 249:1527–1533 (1990)).

The subject is preferably an animal, including, but not limited to, animals such as cows, pigs, horses, chickens, cats, dogs, etc., and is preferably a mammal, and most preferably human.

4.4 Pharmaceutical Compositions

Exemplary means of administration include oral, parenteral, rectal, topical, sublingual, mucosal, nasal, opthalmic, subcutaneous, intramuscular, intravenous, transdermal, spinal, intrathecal, intra articular, intra arterial, sub arachnoid, bronchial, lymphatic, and intrauterine administration.

The present invention contemplates the use of pharmaceutical formulations for human medical use which comprise the vector structures of the present invention as therapeutic ingredients. Such pharmaceutical formulations may include pharmaceutically effective carriers, and optionally, may include other therapeutic ingredients. The carrier or carriers must be pharmaceutically acceptable in the sense that they are compatible with the therapeutic ingredients and are not unduly deleterious to the recipient thereof. The therapeutic ingredient or ingredients are provided in an amount necessary to achieve the desired therapeutic effect, described below.

In another aspect, a pharmaceutical composition is provided to comprising (1) a mixture of an enkephalin conjugate according to the present invention wherein the enkephalin peptide has proline or alanine added to its N-terminus and an enkephalin conjugate according to the present invention which does not have a proline or alanine added to the N-terminus, and (2) a pharmaceutical carrier.

Various delivery systems are known and can be used to administer a conjugate of the invention, e.g., encapsulation microcapsules.

As used herein, the term "pharmaceuticallyacceptable" means approved by a regulatory agency of the Federal or a state government or listed in the U.S. Pharmacopoeia or other generally recognized pharmacopoeia for use in animals, and more particularly in humans.

The term "carrier" refers to a diluent, adjuvant, excipient, or vehicle with which the conjugate is administered.

Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions.

Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol and the like.

The composition, if desired, can also contain minor amounts of wetting or emulsifying agents, or pH buffering agents.

The compositions can take the form of solutions, suspensions, emulsion,-tablets, pills, capsules, powders, sustained release formulations and the like. The composition can be formulated as a suppository, with traditional binders and carriers such as triglycerides.

Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin.

Such compositions will contain a therapeutically effective amount of the drug oligomer conjugate, preferably in purified form, together with a suitable amount of carrier so as to provide the form for proper administration to the patient. The formulation should suit the mode of administration.

The mode of administration and dosage forms will of course affect the therapeutic amounts of the compounds which are desirable and efficacious for the given treatment application. A therapeutically effective amount is an amount necessary to prevent, delay or reduce the severity of the onset of disease, or an amount necessary to arrest or reduce the severity of an ongoing disease. It will be readily apparent to one of skill in the art that this amount will vary based on factors such as the weight and health of the recipient, the type of cells being transformed, the mode of administration of the present compositions and the type of medical disorder being treated.

The dosage can be presented in the form of tablets, syrups, losenges elixirs, suspensions, and/or emulsions.

Accessory ingredients may, without limitation, include diluents, buffers, flavoring agents, disintegrants, surfactants, thickeners, lubricants, preservatives, and/or antioxidants.

In a preferred embodiment, the composition is formulated in accordance with routine procedures as a pharmaceutical composition adapted for intravenous administration to human beings.

Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent.

Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The conjugates of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The amount of the Conjugate of the invention which will be therapeutically effective in the treatment of a particular disorder or condition will depend on the nature of the disorder or condition, and can be determined by standard clinical techniques. In addition, in vivo and/or in vitro assays may optionally be employed to help identify optimal dosage ranges.

For example, suitable doses of a an enkephalin conjugate for analgesia may generally be in the range of from 1 mg/kg to 20 mg/kg, preferably 3 mg/kg to 15 mg/kg, more preferably 5mg/kg to 7 mg/kg.

Effective doses may be extrapolated from dose response curves derived from in vitro or animal model test systems.

Suppositories generally contain active ingredient in the range of 0.5% to 10% by weight; oral formulations preferably contain 10% to 95% active ingredient.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture use or sale for human administration.

The present invention is not to be limited in scope by the specific embodiments described herein. Indeed, various modifications of the invention in addition to those described herein will become apparent to those skilled in the art from the foregoing description and accompanying FIG. 5. Such modifications are intended to fall within the scope of the appended claims.

5. EXAMPLES 5.1 Synthesis 5.1.1 Triethylene Glycol Monohexadecyl Ester

Palmitic anhydride (5.00 g; 10.104 mmol) was dissolved in dry THF (20 mL) and 3 mol excess of dry pyridine and the solution was stirred at room temperature. To the stirring solution, triethylene glycol (1.5 g; 10.104 mmol) was added slowly. After stirring for 1 h, THF was removed under reduced pressure at room temperature and the reaction mixture was poured into ice cold 10% sulfuric acid. The aqueous layer was extracted with ethyl acetate (30 ml×3). Combined organic layer was'sequentially washed with water, brine and dried over $MgSO_4$ and filtered. After evaporation gave pure product, single spot on TLC.

5.1.2 Succinimidyll Triethylene Glycol Monohexadecyl Ester

To a stirring solution of teg palmitate (1 g; 2.57 mmol), dimethylaminopyridine (0.313 g; 2:57mmol) in dry THF was added N,N'-disuccinimidyl carbonate (0.691 g) in one portion. The reaction mixture was stirred overnight at room temperature. The organic solvent was removed under reduced pressure and reaction mixture was diluted with ethyl acetate, washed with 1N hydrochloric acid (10 mL×2), water and brine. The solvent was dried over $MgSO_4$, filtered and evaporated to leave white solid.

5.1.2.1 Determination of Activity

The succinimidyl reactivity was determined by conjugating it with insulin and it was found to be 67%.

5.1.3 Succinimidyl Triethylene Glycol Monohexadecyl Ether

To a cold stirring solution of phosgene (10.0 mL; 20% solution in toluene) under nitrogen, a solution of triethylene glycol monohexadecyl ether (1.5 g; 4.00 mmol) in dry dichloromethane (4 mL) was added. The reaction mixture was stirred at 0° C. for 2 h at room temperature. Excess of phosgene was distilled off using water aspirator, passing through cold solution of dilute NaOH.

The reaction flask was cooled in ice bath and equimolar quantity of triethyl amine and a solution of hydroxysuccinimide, dissolved in minimum quantity of THF was added slowly. The reaction mixture was stirred at room temperature for 12 h. The solvent was removed completely at 25° C. and residue was redissolved in ethyl acetate, washed with water, brine, dried over $MgSO_4$ and evaporated to give pure succinimidyl derivative 5.1.3.1 Determination of Activity The succinimidyl reactivity was determined by conjugating it with insulin and it was found to be 62.5%.

5.2 Conjugation of Compound 2 & 4 with [MET-Enkephlin] MET-Enkephalin 5.2.1 General Procedure for Conjugation

5.2.1.1 SCHEME

NH$_2$-Tyr ... Met-enk   +   Palm-teg-NSU or Cetyl-Teg-NSU

-continued

Palm-Teg-NH ... Met-enk or Cetyl-Teg-NH enk

5.2;1.2 General Procedure

To a stirring solution of met enkephalin (SEQ ID NO:48) (0.130 g; 0.1854 mmol) in 5 mL of DMF-DCM (2:1) was added TEA (25 µL). The reaction mixture was cooled to 10° C. and a solution of palmityl-teg-nsu or cetyl-teg-nsu dissolved in 1 mL of DCM was added in one portion. The reaction mixture was stirred for 2 h at 10° C. The solvent was removed under reduced pressure and the residue was redissolved in dry ethyl acetate. After evaporation of the solvent 0.310 g conjugated enkephalin was obtained. HPLC showed mono & diconjugate in the ratio of 3:1.

5.3 Synthesis of Cetyl-Peg$_2$; it's Activation & Conjugation with Protected (BOC) Leuenk To a suspension of NaH (4.00 g; 0.1 mol) in dry THF (300 mL) at 10° C. was added diethylene glycol in one portion. The cooling bath was removed and reaction mixture was stirred at room temperature for 2 h. At the end of the reaction mixture was cooled to 10° C. and bromohexadecane (29 g; 0.095 mol) was added in one portion. The cooling bath was removed and the reaction was stirred at room temperature for 4 h. The solvent was removed under reduced pressure and crude was admixed with water and extracted with ethyl acetate (30 mL×3). The combined organic extract was sequentially washed with water, brine, dried over MgSO$_4$ and evaporated to leave white solid powder, single spot on TLC and single molecular ion peak.

5.3.1 Cetyl-PEG2-NSU

To a cold stirring solution of phosgene (10.0 mL; 20% solution in toluene) under nitrogen, a solution of cetyl-PEG$_2$-OH (1.3 g; 4.00 mmol) in dry dichloromethane (5 mL) was added. The reaction mixture was stirred at 0° for 1 hr and 2 h at room temperature. Excess of phosgene was distilled off using water aspirator, passing through cold solution of dilute NaOH.

The reaction flask was cooled in ice bath and equimolar quantity of triethyl amine and a solution of hydroxy succinimide, dissolved in minimum quantity of THF was added slowly. The reaction mixture was stirred at room temperature for 12 h. The solvent was removed completely at 25° C. and residue was redissolved in ethyl acetate, washed with water, brine, dried over MgSO$_4$ and evaporated to give pure succinimidyl derivative.

5.3.2 Determination of Activity

The succinimidyl reactivity was determined by conjugating it with insulin and it was found to be 83.5%.

5.4 Conjugation of Succinimidyl Cetyl-PEG2 with BOC-LEU . . . ENK . . . LYS-OH (SEQ ID NO:51)

Boc-Leu . . . enk . . . Lys-OH (SEQ ID NO:51) (100mg; 0.125 mmol) was dissolved in 5 mL of DMF:DCM(1:1) and stirred at 10° C. under nitrogen. To this clear solution TEA (17.5 µL) and a solution of succinimidyl cetyl-PEG$_2$, dissolved in 1 mL of DCM were added.

After 1.5 h (TLC showed single product) the solvent was removed under reduced pressure at room temperature and reaction mixture was admixed with water and extracted with ethyl acetate (10 mL×3). The organic extract was sequentially washed with water, brine, dried and evaporated to a solid.

5.4.1 Purification of Derivatized BOC-LEU . . . ENK . . . LYS-OH (SEQ ID NO:51) on Silica Gel Column The derivatized blocked enkephalin was purified on silica gel column using methanol-chloroform (5% methanol-chloroform) mixture as an eluting solvent. After evaporation of desired fraction 100 mg pure compound was obtained. A product yield of 100 mg was obtained after removal of the solvent.

5.4.2 Deblocking of Butyloxycarbonyl Group from Derivatized LEU . . . ENK (SEQ ID NO:52)

Derivatized Boc-Leu . . . enk (SEQ ID NO:52) (100 mg; 0.0866 mmol) was treated with 0.4ml of TFA-DCM (1: 1) for 30 min. at room temperature. The solvent was removed under reduced pressure. The solid was redissolved in 2 mL of methanol, filtered and evaporated; 80 mg of pure product was obtained.

5.5 Synthesis of Amphiphilic Oligomer-Enkephalin Conjugates

5.5.1 A General Scheme for Synthesis of Non-hydrolyzable and Hydrolyzable Conjugates One hundred milligrams of enkephalin (100 mg; 0.142 mmmol) was dissolved in dry dimethylformamide (5 mL) at room temperature. P-nitrophenol or N-hydroxysuccinimide activated (carbonate or ester) of amphiphilic oligomer (1.1 mole equivalent) was dissolved in 1 mL tetrahydrofuran and added to above solution and stirred at room temperature over 1.5 hours. The extent of the reaction was monitored by a reverse phase (C- 18) HPLC using isopropanol/water (0.1% trifluoroacetic acid) gradient system. Reaction mixture was evaporated under reduced pressure and the contents were dissolved in an isopropanol water mixture. This mixture was purified on a 22 mm preparative HPLC column (C-8) with a solvent gradient system made of either isopropanol/water (0.1% trifluoroacetic acid) or acetonitrile/water (0.1% trifluoroacetic acid to give pure monoconjugated and diconjugated enkephalins. The solvent was evaporated at low temperature (<20° C.) to give dry produce. The purity of the product was analyzed by reverse phase analytical HPLC, and the MW information was obtained by MALDI (TOF)-mass spectral technique.

5.5.2 Synthesis of Cholesterol-PEG$_2$ Hydrolyzable Amphilphilic Oligomer

PEG$_2$ diacid (3,6;9trioxaundecanoic diacid, 10 g) was dissolved in dry chloroform(50 mL) and added dropwise to oxalychloride at room temperature under dry condition in the presence, of catalytic amount of dimethylformamide. The reaction was stirred for 6 hours and the solvent and excess of reagent was stripped off to give an oily residue.

Above residue was dissolved in chloroform (50 mL) and to this was added cholesterol (1.05 mole equivalent) in chloroform (50 mL) and triethylamine (1 mole equivalent) over 30 minutes at 5° C. The reaction was stirred at 15° C. over 2 hours. To this was added N-hydroxysuccinimide (1 mole equivalent) in chloroform (50 mL) and followed by triethylamin (1 equivalent) at 5° C. and allowed to stir overnight. Solvent was stripped off and the product was extracted with ethylacetate. Crude product was purified on a silica gel column with 1:10 methanol/chloroform solvent system to obtain activated amphiphilic oligomer in 80% yield.

5.6 Molecular Weight Information of Enkephalin Conjugates Obtained by Maldi (TOF)-MS

| Enkephalin Conjugate | Expected M. W. | Observed M. W. |
|---|---|---|
| Cholesterol-PEG$_2$ | 1274 | 1275 |
| DHA-PEG$_2$ | 1144.4 | 1144.3 |
| Linolenic-PEG$_2$ | 1093.4 | 1093.3 |
| Cetyl-PEG$_2$ | Avg. 1059 | Avg. 1032 |
| Palmitate-PEG$_3$ | 1116 | 1115.6 |
| Cetyl-PEG$_3$ | 1101 | 1101.12 |

These results demonstrate that the reactions resulted in monoconjugates, i.e., each peptide was coupled to only one oligomer. It is significant to note that a single conjugate is sufficient to impart amphiphilic properties.

5.7 Stability of MET Enkephalin-LYS (SEQ ID NO:49) (Enkephalin) and its Amphiphilic Oligomer Conjugates in Rat Brain Homogenate Met enkephalin lys (SEQ ID NO:49) and its conjugates (Cetyl-PEG$_2$, Cetyl-PEG$_3$ and Palmitate-PEG$_3$) were incubated in 2% rat brain homogenate. Samples were drawn over time intervals and the amount of the substance remaining was measured by a HPLC method. Following experimental procedure was used for the study.

Procedure: A 2% rat brain homogenate was prepared by homogenizing freshly perfused (PBS buffer) rat brain in PBS buffer (pH 7.4). Two 3 mL aliquots of the homogenate were equilibrated at 37° C. in a water bath. To one unmodified enkephalin was added to other modified (conjugate) was added, resulting in a final concentration of 60 µg/mL of peptide. At time 0, 1, 2, 3, 5, 15, 30, and 60 minutes, 200 µL of aliquot was withdrawn and quenched with 200 µL of the quenching agent (1% trifluoroacetic acid in acetonitrile/isopropanol or 1% trichloroacetic acid in water). The sample solutions were vortexed and centrifuged at 7000 RPM. The supernatant was analyzed by a HPLC method using a gradient of 10 to 100% isopropanol/water (0.1% trifluoroacetic acid) on a C-18 column.

FIG. 2 shows the stability of the cetyl-PEG$_2$enkephalin (SEQ ID NO:1) conjugate as compared to free met enkephalin lys (SEQ ID NO:49). FIG. 3 shows the stability of the cetyl-PEG$_3$enkephalin (SEQ ID NO:1) as compared to met-enkephalin-lysine (SEQ ID NO:49). FIG. 4 shows palmitate-PEG$_3$-enk (SEQ ID NO:1) (hydrolyzable) conjugate as compared to met-enkephalin-lys (SEQ ID NO:49).

5.7 Extraction and Detection of Enkephalin Conjugates from the Brain of Dosed Ras

5.7.1.1 Procedure

The following procedure was used to identify the presence of conjugate from the brain specimen of animals dosed with 5 mg/kg cetyl-PEG$_2$enkephalin (SEQ ID NO:1).

After 10 minutes of dosing, the brain of the animal was perfused with 1.5% trifluoroacetic acid in PBS solution, and the brain was removed and frozen at −70° C. The brain was homogenized with 1 mL of 1.5% trifluoroacetic acid in PBS solution and the homogenate was extracted with acetonitrile/isopropanol solution. The extract was treated with saturated sodium chloride solution and frozen at -20° C. for 2 hours. The organic layer was isolated and centrifuged at 4000 RPM. The supernatant was evaporated and the resulting residue was reconstituted in acetonitrile/isopropanol/water mixture. The reconstituted solution was analyzed by HPLC using a gradient of 10 to 100% isopropanol/water (0.1% trifluoroacetic acid) on a C-18 column. The presence and the concentration of cetyl-PEG$_2$enkephalin (SEQ ID NO:1) conjugate in the extract were measured by comparing the retention time and the peak area of standard solution under the same analytical condition. The results are presented in FIGS. 5A to 5D.

5.7.1.2 Results

Figure 5A:
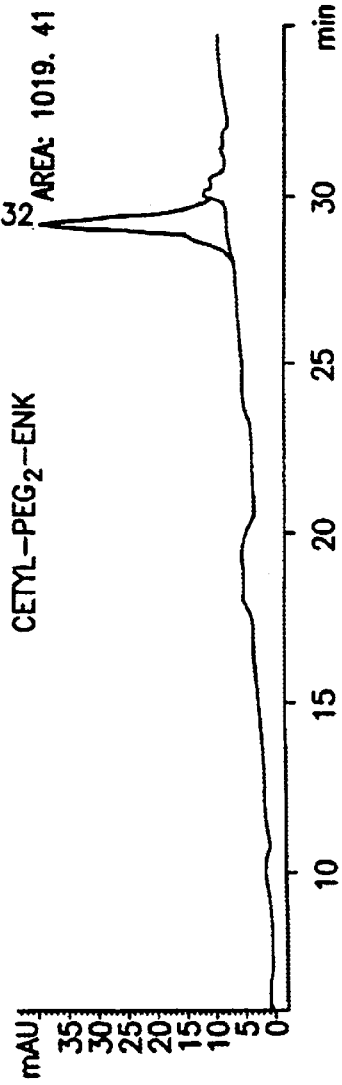
Figure 5B:
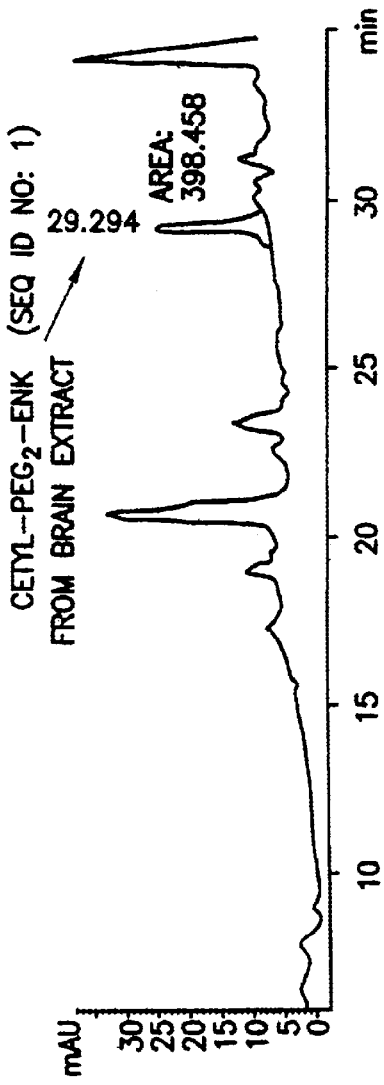
Figure 5C:
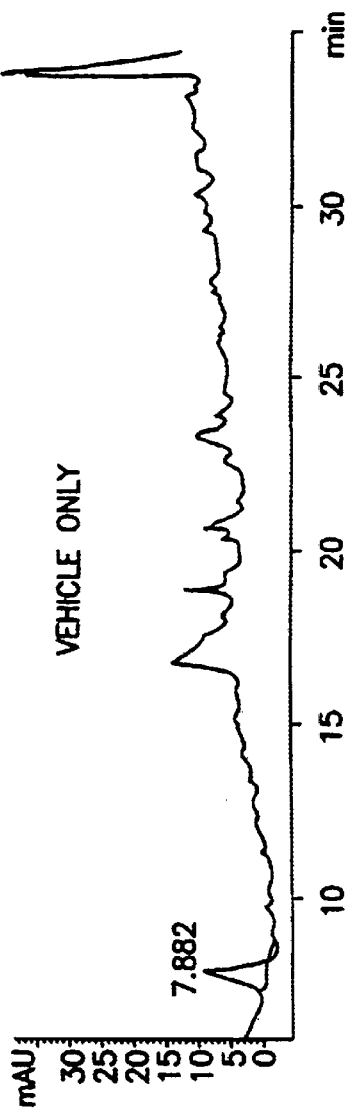
Figure 5D:
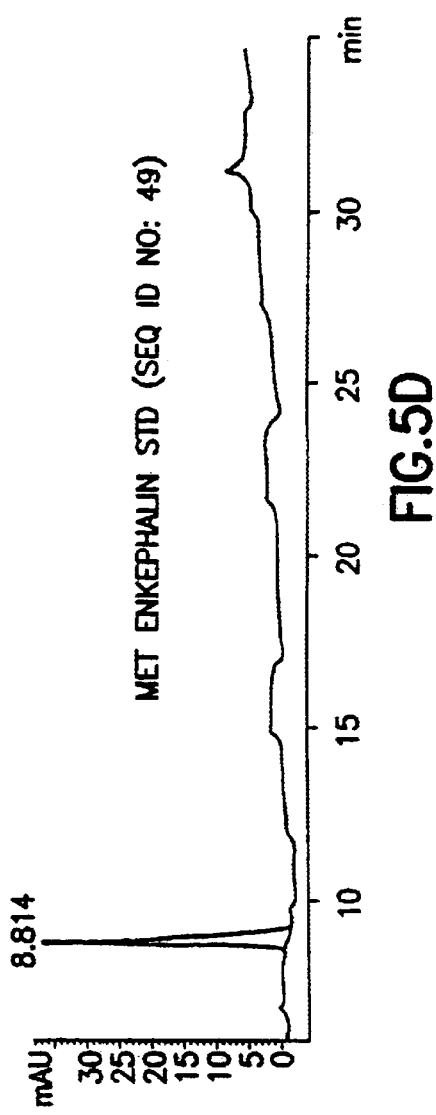

The results demonstrate that monoconjugates were isolated from brain tissue. FIG. 5A shows a peak produced by cetyl enkephalin (SEQ ID NO:1) standard, while 5 B shows a corresponding peach demonstrating that cetyl enkephalin (SEQ ID NO:1) was actually present in the brain extract. In contrast, neither the vehicle (FIG. 5C) nor the unconjugated enkephalin (SEQ ID NO:49) (FIG. 5D) showed a corresponding peak.

5.8 Rat Paw-Hot Plate Test

5.8.1 Animals

Adult, male Sprague-Dawley rats weighing 150–175 g were obtained from Charles River Breeding Laboratories (Raleigh, N.C.) and used for all animal studies. Rats were housed in hanging wire bottomed cages in a vivarium equipped with a 12:12 light:dark cycle and humidity was maintained between 45–65% with a room temperature of 72±2° C. Rats were provided Purina Rodent Chow and tap water ad libitum.

5.8.2 Methods

Met-enkephalin-lys (SEQ ID NO:49) and met-enkephalin-lys derivatives (SEQ ID NO:1) were assessed for analgesic activity by rat paw hot plate assay. Rats were given an injection of naloxone at 0.5 mg/kg (s.c.) then administered a single administration of cetyl enkephalin (SEQ ID NO:1l) by the tail vein 10 minutes later at a dose of 5.0 mg/kg. The results as graphically displayed in FIG. 6 demonstrate that Naloxone, an µ-receptor antagonist prevents competitively inhibits binding of cetyl-PEG$_2$-enkephalin (SEQ ID NO:1), thus demonstrating that at least part of the activity of cetyl-PEG$_2$-enkephalin (SEQ ID NO:1) is attributable to binding at the Opioid µ-receptor.

In a separate study, rats were administered cetyl enkephalin (SEQ ID NO:1) (5.0 mg/kg, i.v.) or clonidine (0.125 mg/kg, i.v.).

The latency to rat paw withdrawal from the hot plate was measured by a Hot Plate Analgesia Meter (Harvard Apparatus Ltd., Kent, England). The temperature of the hot plate was set and calibrated at 52° C. and rats were removed from the heat stimulus by 36 seconds after placement. Latency trials were terminated when the animal was either licking a hind paw or initiating a jump from the plate. Baseline measurements were collected 1 hour prior to drug administration and at various times post injection, dependent upon the study conducted. All hot plate testing was terminated by 1 hour after drug dosing.

5.8.3 Results

The results are displayed in the following tables and in the Graph of FIG. 6. The results demonstrate that while 20 mg/kg enkephalin (SEQ ID NO:49) alone has 0% analgesic effect as compared to morphine as a baseline, the enkephalin conjugates of the present invention had strong analgesic effects and one conjugate, DHA-PEG-ENK (SEQ ID NO:1) had 130% of the analgesic effect of morphine. The graph of FIG. 7 shows that CETYL-PEG-ENK (SEQ ID NO:1) produces a response and duration comparable to that of clonidine, an αα-andrenergic receptor agonist.

| ANALGESIC EFFECT OF ENKEPHALIN CONJUGATES IN RATS | | | | |
|---|---|---|---|---|
| | | | Mean Analgesia as Compared with Morphine at 3 mg/Kg* | |
| | Dose | Number | | |
| Drug or Conjugate | (mg/kg) | of Rats | @ 5 min | @ 30 min |
| Morphine | 3 | 8 | 100% | 100% |
| Enkephalin (SEQ ID NO:49) | 20 | 7 | 0% | 0% |
| Cetyl-PEG-ENK (SEQ ID NO:1) | 5 | 8 | 84% | 75% |
| DHA-PEG-ENK (SEQ ID NO:1) | 20 | 8 | 130% | 67% |
| Cholesterol-PEG-ENK (SEQ ID NO:1) | 5 | 8 | 80% | 68% |
| Linolenic-PEG-ENK (SEQ ID NO:1) | 10 | 8 | 77% | 73% |

5.9 Agonist-stimulate [$^{35}$S] GTPγS Binding in Brain Sections

5.9.1 Materials

Male Sprague-Dawley rats (200 g) were purchased from Zivic-Miller (Zelienople, Pa.). [$^{35}$S]GTPγS (1250 Ci/mmol) was purchased from New England Nuclear Corp. (Boston, Mass.). [D-Ala$^2$, N-Me-Phe$^4$,Gly$^5$-ol]-enkephalin (DAMGO), adenosine deaminase, and GDP were obtained from Sigma Chemical Co. (St. Louis, Mo.). Reflections® autoradiography film was purchased from New England Nuclear Corp. (Boston, Mass.). All other reagent grade chemicals were obtained from Sigma Chemical Co. or Fisher.

5.9.2 Agonist-stimulated [$^{35}$S] GTPγS Binding in Brain Sections

Agonist stimulated [$^{35}$5]GTPγS autoradiography was performed as described by Sim et al. *Proc. Nat'l Acad. Sci.* USA 1992 Pg. 7242–7246. Animals were sacrificed by decapitation and brains were removed and frozen in isopentane at −30° C. Coronal and horizontal brain sections were cut on a cryostat maintained at -20° C. Sections were incubated in assay buffer (50 mM Tris-HCl, 3 mM $MgCl_2$, 0.2 mM EGTA, 100 mM NaCl, pH 7.4) at 25° C. for 10 min. Sections were then incubated in assay buffer containing 2 mM GDP, protease inhibitor cocktail (10 μl/ml of a solution containing 0.2 mg/ml each of bestatin, leupeptin, pepstatin A and aprotinin), and adenosine deaminase (9.5 mU/ml) at 25° C. for 15 min. Section were then incubated in assay buffer with GDP, 0.04 nM [$^{35}$S]GTPγS and appropriate agonist at 25° C. for 2 hours. The agonists were: 10 μM DAMGO, 10 μM cetyl enkephalin (SEQ ID NO:1) and 10 μM cetyl-TEG-enkephalin (SEQ ID NO:1). Basal binding was assessed in the absence of agonist. Slides were rinsed twice for 2 min each in cold Tris buffer (50 mM Tris-HCl, pH 7.4) and once in deionized $H_2O$. Slides were dried overnight and exposed to film for 72 hours. Films were digitized with a Sony XC-77 video camera and analyzed using the NIH IMAGE program for Macintosh computers.

5.9.3 Results

Results show that cetyl-TEG-enkephalin (SEQ ID NO:1) stimulates of [$^{35}$S]GTPγS binding. The anatomical distribution of the binding is consistent with that of μ Opioid receptors. These results demonstrate that cetyl-TEG-enkephalin (SEQ ID NO:1) does not simply bind the receptor but also activates the receptor, causing the receptor to bind to G-protein. This activation provides further corroborative evidence that cetyl-TEG-enkephalin (SEQ ID NO:1) directly stimulates analgesia.

SEQUENCE LISTING

```
<160> NUMBER OF SEQ ID NOS: 52

<210> SEQ ID NO 1
<211> LENGTH: 6
<212> TYPE: PRT
<213> ORGANISM: synthetic construct
<220> FEATURE:
<221> NAME/KEY: MOD_RES
<222> LOCATION: (6)..(6)
<223> OTHER INFORMATION: Polymer connected to epsilon-amino group

<400> SEQUENCE: 1

Tyr Gly Gly Phe Met Lys
1               5

<210> SEQ ID NO 2
<211> LENGTH: 6
<212> TYPE: PRT
<213> ORGANISM: synthetic construct
<220> FEATURE:
<221> NAME/KEY: MOD_RES
<222> LOCATION: (1)..(1)
<223> OTHER INFORMATION: Polymer connected to alpha-amino group
<220> FEATURE:
<221> NAME/KEY: MOD_RES
<222> LOCATION: (6)..(6)
<223> OTHER INFORMATION: Polymer connected to epsilon-amino group

<400> SEQUENCE: 2

Tyr Gly Gly Phe Met Lys
1               5

<210> SEQ ID NO 3
<211> LENGTH: 6
<212> TYPE: PRT
<213> ORGANISM: synthetic construct
<220> FEATURE:
<221> NAME/KEY: MOD_RES
<222> LOCATION: (1)..(1)
<223> OTHER INFORMATION: Polymer connected to alpha-amino group

<400> SEQUENCE: 3

Tyr Gly Gly Phe Met Lys
1               5
```

```
<210> SEQ ID NO 4
<211> LENGTH: 6
<212> TYPE: PRT
<213> ORGANISM: synthetic construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (6)..(6)
<223> OTHER INFORMATION: AMIDATION

<400> SEQUENCE: 4

Phe Arg Trp Trp Tyr Lys
1               5

<210> SEQ ID NO 5
<211> LENGTH: 6
<212> TYPE: PRT
<213> ORGANISM: synthetic construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (6)..(6)
<223> OTHER INFORMATION: AMIDATION

<400> SEQUENCE: 5

Arg Trp Ile Gly Trp Lys
1               5

<210> SEQ ID NO 6
<211> LENGTH: 6
<212> TYPE: PRT
<213> ORGANISM: synthetic construct
<220> FEATURE:
<221> NAME/KEY: MOD_RES
<222> LOCATION: (6)..(6)
<223> OTHER INFORMATION: AMIDATION
<220> FEATURE:
<221> NAME/KEY: UNSURE
<222> LOCATION: (6)..(6)
<223> OTHER INFORMATION: Xaa can be any of the twenty naturally
      occurring amino acids

<400> SEQUENCE: 6

Trp Trp Pro Lys His Xaa
1               5

<210> SEQ ID NO 7
<211> LENGTH: 4
<212> TYPE: PRT
<213> ORGANISM: synthetic construct
<220> FEATURE:
<221> NAME/KEY: MOD_RES
<222> LOCATION: (4)..(4)
<223> OTHER INFORMATION: AMIDATION
<220> FEATURE:
<221> NAME/KEY: UNSURE
<222> LOCATION: (4)..(4)
<223> OTHER INFORMATION: Xaa is either Lys or Arg

<400> SEQUENCE: 7

Trp Trp Pro Xaa
1

<210> SEQ ID NO 8
```

```
<211> LENGTH: 6
<212> TYPE: PRT
<213> ORGANISM: synthetic construct
<220> FEATURE:
<221> NAME/KEY: MOD_RES
<222> LOCATION: (6)..(6)
<223> OTHER INFORMATION: AMIDATION
<220> FEATURE:
<221> NAME/KEY: UNSURE
<222> LOCATION: (6)..(6)
<223> OTHER INFORMATION: Xaa can be any one of the naturally occurring
      amino acids

<400> SEQUENCE: 8

Tyr Pro Phe Gly Phe Xaa
1               5

<210> SEQ ID NO 9
<211> LENGTH: 7
<212> TYPE: PRT
<213> ORGANISM: synthetic construct
<220> FEATURE:
<221> NAME/KEY: MOD_RES
<222> LOCATION: (1)..(5)
<223> OTHER INFORMATION: Amino acids are in the D-form
<220> FEATURE:
<221> NAME/KEY: MOD_RES
<222> LOCATION: (6)..(6)
<223> OTHER INFORMATION: n is 0 or 1
<220> FEATURE:
<221> NAME/KEY: MOD_RES
<222> LOCATION: (7)..(7)
<223> OTHER INFORMATION: Xaa is Gly or the D-form of a naturally
      occurring amino acid
<220> FEATURE:
<221> NAME/KEY: MOD_RES
<222> LOCATION: (7)..(7)
<223> OTHER INFORMATION: AMIDATION

<400> SEQUENCE: 9

Ile Met Ser Trp Trp Gly Xaa
1               5

<210> SEQ ID NO 10
<211> LENGTH: 6
<212> TYPE: PRT
<213> ORGANISM: synthetic construct
<220> FEATURE:
<221> NAME/KEY: MOD_RES
<222> LOCATION: (1)..(4)
<223> OTHER INFORMATION: Amino acids are in the D-form
<220> FEATURE:
<221> NAME/KEY: MOD_RES
<222> LOCATION: (6)..(6)
<223> OTHER INFORMATION: Xaa is Gly or the D-form of a
      naturally-occurring amino acid
<220> FEATURE:
<221> NAME/KEY: MOD_RES
<222> LOCATION: (6)..(6)
<223> OTHER INFORMATION: AMIDATION

<400> SEQUENCE: 10

Ile Met Thr Trp Gly Xaa
1               5

<210> SEQ ID NO 11
<211> LENGTH: 4
<212> TYPE: PRT
<213> ORGANISM: synthetic construct
<220> FEATURE:
<221> NAME/KEY: MOD_RES
<222> LOCATION: (2)..(2)
<223> OTHER INFORMATION: Xaa is A1, wherein A1 is the D-form of Nve or
```

```
        Nle
<220> FEATURE:
<221> NAME/KEY: MOD_RES
<222> LOCATION: (3)..(3)
<223> OTHER INFORMATION: Xaa  is B2, wherein B2 is Gly, Phe, or Trp
<220> FEATURE:
<221> NAME/KEY: MOD_RES
<222> LOCATION: (4)..(4)
<223> OTHER INFORMATION: Xaa is C3, wherein C3 is Trp or Nap
<220> FEATURE:
<221> NAME/KEY: MOD_RES
<222> LOCATION: (4)..(4)
<223> OTHER INFORMATION: AMIDATION

<400> SEQUENCE: 11

Tyr Xaa Xaa Xaa
1

<210> SEQ ID NO 12
<211> LENGTH: 3
<212> TYPE: PRT
<213> ORGANISM: synthetic construct
<220> FEATURE:
<221> NAME/KEY: MOD_RES
<222> LOCATION: (1)..(1)
<223> OTHER INFORMATION: Tyr has at its N-terminus an Me-x-H-y-N group,
      wherein x is 0, 1, or 2; and y is 0, 1, or 2, with the proviso
      that x and y is never greater than
<220> FEATURE:
<221> NAME/KEY: MOD_RES
<222> LOCATION: (1)..(2)
<223> OTHER INFORMATION: The amine between the first Tyr and the second
      Tyr is methylated
<220> FEATURE:
<221> NAME/KEY: MOD_RES
<222> LOCATION: (3)..(3)
<223> OTHER INFORMATION: Xaa is Xaa-z, wherein Xaa is Phe, (D)Phe, or
      NHBzl, and wherein z is 0 or
<220> FEATURE:
<221> NAME/KEY: MOD_RES
<222> LOCATION: (3)..(3)
<223> OTHER INFORMATION: AMIDATION

<400> SEQUENCE: 12

Tyr Tyr Xaa
1

<210> SEQ ID NO 13
<211> LENGTH: 6
<212> TYPE: PRT
<213> ORGANISM: synthetic construct
<220> FEATURE:
<221> NAME/KEY: MOD_RES
<222> LOCATION: (4)..(4)
<223> OTHER INFORMATION: Xaa is D4, wherein D4 is Lys or Arg
<220> FEATURE:
<221> NAME/KEY: MOD_RES
<222> LOCATION: (5)..(5)
<223> OTHER INFORMATION: His is His-z, wherein z is 0 or 1
<220> FEATURE:
<221> NAME/KEY: MOD_RES
<222> LOCATION: (6)..(6)
<223> OTHER INFORMATION: Xaa is Xaa-z, wherein Xaa is a naturally
      occurring amino acid and z is 0 or
<220> FEATURE:
<221> NAME/KEY: MOD_RES
<222> LOCATION: (6)..(6)
<223> OTHER INFORMATION: AMIDATION

<400> SEQUENCE: 13

Trp Trp Pro Xaa His Xaa
1               5
```

```
<210> SEQ ID NO 14
<211> LENGTH: 4
<212> TYPE: PRT
<213> ORGANISM: synthetic construct
<220> FEATURE:
<221> NAME/KEY: MOD_RES
<222> LOCATION: (2)..(2)
<223> OTHER INFORMATION: Xaa is Tic, i.e. 1,2,3,4-tetrahydroisoquinoline
      -3-carboxylic acid

<400> SEQUENCE: 14

Tyr Xaa Phe Phe
1

<210> SEQ ID NO 15
<211> LENGTH: 4
<212> TYPE: PRT
<213> ORGANISM: synthetic construct
<220> FEATURE:
<221> NAME/KEY: MOD_RES
<222> LOCATION: (2)..(2)
<223> OTHER INFORMATION: Xaa is Tic, i.e. 1,2,3,4-tetrahydroisoquinoline
      -3-carboxylic acid
<220> FEATURE:
<221> NAME/KEY: MOD_RES
<222> LOCATION: (4)..(4)
<223> OTHER INFORMATION: AMIDATION

<400> SEQUENCE: 15

Tyr Xaa Phe Phe
1

<210> SEQ ID NO 16
<211> LENGTH: 4
<212> TYPE: PRT
<213> ORGANISM: synthetic construct
<220> FEATURE:
<221> NAME/KEY: MOD_RES
<222> LOCATION: (1)..(1)
<223> OTHER INFORMATION: Tyr is Tyr(N-alpha-Me), i.e. N-alpha
      -methyltyrosine
<220> FEATURE:
<221> NAME/KEY: MOD_RES
<222> LOCATION: (2)..(2)
<223> OTHER INFORMATION: Xaa is Tic, i.e. 1,2,3,4-tetrahydroisoquinoline
      -3-carboxylic acid

<400> SEQUENCE: 16

Tyr Xaa Phe Phe
1

<210> SEQ ID NO 17
<211> LENGTH: 4
<212> TYPE: PRT
<213> ORGANISM: synthetic construct
<220> FEATURE:
<221> NAME/KEY: MOD_RES
<222> LOCATION: (1)..(1)
<223> OTHER INFORMATION: Tyr is Tyr(N-alpha-Cmp), i.e. N-alpha
      -cyclopropylmethyltyrosine
<220> FEATURE:
<221> NAME/KEY: MOD_RES
<222> LOCATION: (2)..(2)
<223> OTHER INFORMATION: Xaa is Tic, i.e. 1,2,3,4-tetrahydroisoquinoline
      -3-carboxylic acid

<400> SEQUENCE: 17

Tyr Xaa Phe Phe
1

<210> SEQ ID NO 18
```

```
<211> LENGTH: 4
<212> TYPE: PRT
<213> ORGANISM: synthetic construct
<220> FEATURE:
<221> NAME/KEY: MOD_RES
<222> LOCATION: (1)..(1)
<223> OTHER INFORMATION: Tyr is Tyr(N-alpha-Hex), i.e. N-alpha
      -hexyltyrosine
<220> FEATURE:
<221> NAME/KEY: MOD_RES
<222> LOCATION: (2)..(2)
<223> OTHER INFORMATION: Xaa is Tic, i.e. 1,2,3,4-tetrahydroisoquinoline
      -3-carboxylic acid

<400> SEQUENCE: 18

Tyr Xaa Phe Phe
1

<210> SEQ ID NO 19
<211> LENGTH: 4
<212> TYPE: PRT
<213> ORGANISM: synthetic construct
<220> FEATURE:
<221> NAME/KEY: MOD_RES
<222> LOCATION: (1)..(1)
<223> OTHER INFORMATION: Tyr is Tyr(N-alpha-Et2), i.e. N-alpha
      -diethyltyrosine
<220> FEATURE:
<221> NAME/KEY: MOD_RES
<222> LOCATION: (2)..(2)
<223> OTHER INFORMATION: Xaa is Tic, i.e. 1,2,3,4-tetrahydroisoquinoline
      -3-carboxylic acid

<400> SEQUENCE: 19

Tyr Xaa Phe Phe
1

<210> SEQ ID NO 20
<211> LENGTH: 4
<212> TYPE: PRT
<213> ORGANISM: synthetic construct
<220> FEATURE:
<221> NAME/KEY: MOD_RES
<222> LOCATION: (1)..(1)
<223> OTHER INFORMATION: Tyr is Dmt, i.e. 2,6-dimethyltyrosine
<220> FEATURE:
<221> NAME/KEY: MOD_RES
<222> LOCATION: (2)..(2)
<223> OTHER INFORMATION: Xaa is Tic, i.e. 1,2,3,4-tetrahydroisoquinoline
      -3-carboxylic acid

<400> SEQUENCE: 20

Tyr Xaa Phe Phe
1

<210> SEQ ID NO 21
<211> LENGTH: 4
<212> TYPE: PRT
<213> ORGANISM: synthetic construct
<220> FEATURE:
<221> NAME/KEY: MOD_RES
<222> LOCATION: (1)..(1)
<223> OTHER INFORMATION: Tyr is Dmt, i.e. 2,6-dimethyltyrosine
<220> FEATURE:
<221> NAME/KEY: MOD_RES
<222> LOCATION: (2)..(2)
<223> OTHER INFORMATION: Xaa is Tic, i.e. 1,2,3,4-tetrahydroisoquinoline
      -3-carboxylic acid
<220> FEATURE:
<221> NAME/KEY: MOD_RES
<222> LOCATION: (4)..(4)
<223> OTHER INFORMATION: AMIDATION
```

```
<400> SEQUENCE: 21

Tyr Xaa Phe Phe
1

<210> SEQ ID NO 22
<211> LENGTH: 4
<212> TYPE: PRT
<213> ORGANISM: synthetic construct
<220> FEATURE:
<221> NAME/KEY: MOD_RES
<222> LOCATION: (1)..(1)
<223> OTHER INFORMATION: Tyr is H-Tyr(3-F), i.e. 3-fluorotyrosine
<220> FEATURE:
<221> NAME/KEY: MOD_RES
<222> LOCATION: (2)..(2)
<223> OTHER INFORMATION: Xaa is Tic, i.e. 1,2,3,4-tetrahydroisoquinoline
      -3-carboxylic acid

<400> SEQUENCE: 22

Tyr Xaa Phe Phe
1

<210> SEQ ID NO 23
<211> LENGTH: 4
<212> TYPE: PRT
<213> ORGANISM: synthetic construct
<220> FEATURE:
<221> NAME/KEY: MOD_RES
<222> LOCATION: (1)..(1)
<223> OTHER INFORMATION: Tyr is H-Tyr(3-Cl), i.e. 3-Chlorotyrosine
<220> FEATURE:
<221> NAME/KEY: MOD_RES
<222> LOCATION: (2)..(2)
<223> OTHER INFORMATION: Xaa is Tic, i.e. 1,2,3,4-tetrahydroisoquinoline
      -3-carboxylic acid

<400> SEQUENCE: 23

Tyr Xaa Phe Phe
1

<210> SEQ ID NO 24
<211> LENGTH: 4
<212> TYPE: PRT
<213> ORGANISM: synthetic construct
<220> FEATURE:
<221> NAME/KEY: MOD_RES
<222> LOCATION: (1)..(1)
<223> OTHER INFORMATION: Tyr is H-Tyr(3-Br), i.e. 3-bromotyrosine
<220> FEATURE:
<221> NAME/KEY: MOD_RES
<222> LOCATION: (2)..(2)
<223> OTHER INFORMATION: Xaa is Tic, i.e. 1,2,3,4-tetrahydroisoquinoline
      -3-carboxylic acid

<400> SEQUENCE: 24

Tyr Xaa Phe Phe
1

<210> SEQ ID NO 25
<211> LENGTH: 4
<212> TYPE: PRT
<213> ORGANISM: synthetic construct
<220> FEATURE:
<221> NAME/KEY: MOD_RES
<222> LOCATION: (1)..(1)
<223> OTHER INFORMATION: Tyr is Dmt, i.e. 2,6-dimethyltyrosine
<220> FEATURE:
<221> NAME/KEY: MOD_RES
<222> LOCATION: (2)..(2)
<223> OTHER INFORMATION: Xaa is Tic-psi-[CH2-], i.e. 3-methyl-1,2,3,4
      -tetrahydroisoquinolin
```

```
<220> FEATURE:
<221> NAME/KEY: MOD_RES
<222> LOCATION: (2)..(3)
<223> OTHER INFORMATION: nonpeptidyl bond

<400> SEQUENCE: 25

Tyr Xaa Phe Phe
1

<210> SEQ ID NO 26
<211> LENGTH: 4
<212> TYPE: PRT
<213> ORGANISM: synthetic construct
<220> FEATURE:
<221> NAME/KEY: MOD_RES
<222> LOCATION: (1)..(1)
<223> OTHER INFORMATION: Tyr is Dmt, i.e. 2,6-dimethyltyrosine
<220> FEATURE:
<221> NAME/KEY: MOD_RES
<222> LOCATION: (2)..(3)
<223> OTHER INFORMATION: nonpeptidyl bond
<220> FEATURE:
<221> NAME/KEY: MOD_RES
<222> LOCATION: (2)..(2)
<223> OTHER INFORMATION: Xaa is Tic-psi-[CH2-], i.e. 3-methyl-1,2,3,4
     -tetrahydroisoquinolin
<220> FEATURE:
<221> NAME/KEY: MOD_RES
<222> LOCATION: (4)..(4)
<223> OTHER INFORMATION: AMIDATION

<400> SEQUENCE: 26

Tyr Xaa Phe Phe
1

<210> SEQ ID NO 27
<211> LENGTH: 4
<212> TYPE: PRT
<213> ORGANISM: synthetic construct
<220> FEATURE:
<221> NAME/KEY: MOD_RES
<222> LOCATION: (2)..(2)
<223> OTHER INFORMATION: Xaa is Tic-psi-[CH2-], i.e. 3-methyl-1,2,3,4
     -tetrahydroisoquinolin
<220> FEATURE:
<221> NAME/KEY: MOD_RES
<222> LOCATION: (3)..(3)
<223> OTHER INFORMATION: Phe is -NCH3]Phe, i.e. N-methylphenylalanine

<400> SEQUENCE: 27

Tyr Xaa Phe Phe
1

<210> SEQ ID NO 28
<211> LENGTH: 4
<212> TYPE: PRT
<213> ORGANISM: synthetic construct
<220> FEATURE:
<221> NAME/KEY: MOD_RES
<222> LOCATION: (2)..(2)
<223> OTHER INFORMATION: Xaa is Tic-psi-[CH2-], i.e. 3-methyl-1,2,3,4
     -tetrahydroisoquinolin
<220> FEATURE:
<221> NAME/KEY: MOD_RES
<222> LOCATION: (3)..(3)
<223> OTHER INFORMATION: Phe is -NH]Hfe, i.e. homophenylalanine

<400> SEQUENCE: 28

Tyr Xaa Phe Phe
1
```

```
<210> SEQ ID NO 29
<211> LENGTH: 4
<212> TYPE: PRT
<213> ORGANISM: synthetic construct
<220> FEATURE:
<221> NAME/KEY: MOD_RES
<222> LOCATION: (1)..(1)
<223> OTHER INFORMATION: Tyr is Tyr(NMe), i.e. N-methyltyrosine
<220> FEATURE:
<221> NAME/KEY: MOD_RES
<222> LOCATION: (2)..(2)
<223> OTHER INFORMATION: Xaa is Tic-psi-[CH2-], i.e. 3-methyl-1,2,3,4
      -tetrahydroisoquinolin
<220> FEATURE:
<221> NAME/KEY: MOD_RES
<222> LOCATION: (3)..(3)
<223> OTHER INFORMATION: Phe is -NH]Hfe, i.e. homophenylalanine

<400> SEQUENCE: 29

Tyr Xaa Phe Phe
1

<210> SEQ ID NO 30
<211> LENGTH: 4
<212> TYPE: PRT
<213> ORGANISM: synthetic construct
<220> FEATURE:
<221> NAME/KEY: MOD_RES
<222> LOCATION: (2)..(2)
<223> OTHER INFORMATION: Xaa is Tic, i.e. 1,2,3,4-tetrahydroisoquinoline
      -3-carboxylic acid
<220> FEATURE:
<221> NAME/KEY: MOD_RES
<222> LOCATION: (3)..(3)
<223> OTHER INFORMATION: Gly is Phg, i.e. phenylglycine

<400> SEQUENCE: 30

Tyr Xaa Gly Phe
1

<210> SEQ ID NO 31
<211> LENGTH: 4
<212> TYPE: PRT
<213> ORGANISM: synthetic construct
<220> FEATURE:
<221> NAME/KEY: MOD_RES
<222> LOCATION: (2)..(2)
<223> OTHER INFORMATION: Xaa is Tic, i.e. 1,2,3,4-tetrahydroisoquinoline
      -3-carboxylic acid

<400> SEQUENCE: 31

Tyr Xaa Trp Phe
1

<210> SEQ ID NO 32
<211> LENGTH: 4
<212> TYPE: PRT
<213> ORGANISM: synthetic construct
<220> FEATURE:
<221> NAME/KEY: MOD_RES
<222> LOCATION: (2)..(2)
<223> OTHER INFORMATION: Xaa is Tic, i.e. 1,2,3,4-tetrahydroisoquinoline
      -3-carboxylic acid
<220> FEATURE:
<221> NAME/KEY: MOD_RES
<222> LOCATION: (4)..(4)
<223> OTHER INFORMATION: AMIDATION

<400> SEQUENCE: 32

Tyr Xaa Trp Phe
1
```

```
<210> SEQ ID NO 33
<211> LENGTH: 4
<212> TYPE: PRT
<213> ORGANISM: synthetic construct
<220> FEATURE:
<221> NAME/KEY: MOD_RES
<222> LOCATION: (2)..(2)
<223> OTHER INFORMATION: Xaa is Tic, i.e. 1,2,3,4-tetrahydroisoquinoline
      -3-carboxylic acid

<400> SEQUENCE: 33

Tyr Xaa His Phe
1

<210> SEQ ID NO 34
<211> LENGTH: 4
<212> TYPE: PRT
<213> ORGANISM: synthetic construct
<220> FEATURE:
<221> NAME/KEY: MOD_RES
<222> LOCATION: (2)..(2)
<223> OTHER INFORMATION: Xaa is Tic, i.e. 1,2,3,4-tetrahydroisoquinoline
      -3-carboxylic acid
<220> FEATURE:
<221> NAME/KEY: MOD_RES
<222> LOCATION: (3)..(3)
<223> OTHER INFORMATION: Ala is 2-Nal, i.e. 3-(2'-naphthyl)alanine

<400> SEQUENCE: 34

Tyr Xaa Ala Phe
1

<210> SEQ ID NO 35
<211> LENGTH: 4
<212> TYPE: PRT
<213> ORGANISM: synthetic construct
<220> FEATURE:
<221> NAME/KEY: MOD_RES
<222> LOCATION: (2)..(2)
<223> OTHER INFORMATION: Xaa is Tic, i.e. 1,2,3,4-tetrahydroisoquinoline
      -3-carboxylic acid
<220> FEATURE:
<221> NAME/KEY: MOD_RES
<222> LOCATION: (3)..(3)
<223> OTHER INFORMATION: Xaa is Atc, i.e. 2-aminotetralin-2-carboxylic
      acid

<400> SEQUENCE: 35

Tyr Xaa Xaa Phe
1

<210> SEQ ID NO 36
<211> LENGTH: 4
<212> TYPE: PRT
<213> ORGANISM: synthetic construct
<220> FEATURE:
<221> NAME/KEY: MOD_RES
<222> LOCATION: (2)..(2)
<223> OTHER INFORMATION: Xaa is Tic, i.e. 1,2,3,4-tetrahydroisoquinoline
      -3-carboxylic acid
<220> FEATURE:
<221> NAME/KEY: MOD_RES
<222> LOCATION: (4)..(4)
<223> OTHER INFORMATION: Phe is Phe(pNO2), i.e. 4-nitrophenylalanine

<400> SEQUENCE: 36

Tyr Xaa Phe Phe
1

<210> SEQ ID NO 37
```

```
<211> LENGTH: 4
<212> TYPE: PRT
<213> ORGANISM: synthetic construct
<220> FEATURE:
<221> NAME/KEY: MOD_RES
<222> LOCATION: (2)..(2)
<223> OTHER INFORMATION: Xaa is Tic, i.e. 1,2,3,4-tetrahydroisoquinoline
      -3-carboxylic acid
<220> FEATURE:
<221> NAME/KEY: MOD_RES
<222> LOCATION: (4)..(4)
<223> OTHER INFORMATION: Phe is Phe(pNO2), i.e. 4-nitrophenylalanine

<400> SEQUENCE: 37

Tyr Xaa Trp Phe
1

<210> SEQ ID NO 38
<211> LENGTH: 4
<212> TYPE: PRT
<213> ORGANISM: synthetic construct
<220> FEATURE:
<221> NAME/KEY: MOD_RES
<222> LOCATION: (2)..(2)
<223> OTHER INFORMATION: Xaa is Tic, i.e. 1,2,3,4-tetrahydroisoquinoline
      -3-carboxylic acid
<220> FEATURE:
<221> NAME/KEY: MOD_RES
<222> LOCATION: (4)..(4)
<223> OTHER INFORMATION: AMIDATION

<400> SEQUENCE: 38

Tyr Xaa Phe Trp
1

<210> SEQ ID NO 39
<211> LENGTH: 7
<212> TYPE: PRT
<213> ORGANISM: synthetic construct
<220> FEATURE:
<221> NAME/KEY: MOD_RES
<222> LOCATION: (2)..(2)
<223> OTHER INFORMATION: Xaa is Tic, i.e. 1,2,3,4-tetrahydroisoquinoline
      -3-carboxylic acid
<220> FEATURE:
<221> NAME/KEY: MOD_RES
<222> LOCATION: (7)..(7)
<223> OTHER INFORMATION: AMIDATION

<400> SEQUENCE: 39

Tyr Xaa Phe Phe Val Val Gly
1               5

<210> SEQ ID NO 40
<211> LENGTH: 7
<212> TYPE: PRT
<213> ORGANISM: synthetic construct
<220> FEATURE:
<221> NAME/KEY: MOD_RES
<222> LOCATION: (2)..(2)
<223> OTHER INFORMATION: Xaa is Tic, i.e. 1,2,3,4-tetrahydroisoquinoline
      -3-carboxylic acid
<220> FEATURE:
<221> NAME/KEY: MOD_RES
<222> LOCATION: (7)..(7)
<223> OTHER INFORMATION: AMIDATION

<400> SEQUENCE: 40

Tyr Xaa Phe Phe Tyr Pro Ser
1               5
```

```
<210> SEQ ID NO 41
<211> LENGTH: 7
<212> TYPE: PRT
<213> ORGANISM: synthetic construct
<220> FEATURE:
<221> NAME/KEY: MOD_RES
<222> LOCATION: (2)..(2)
<223> OTHER INFORMATION: Xaa is Tic, i.e. 1,2,3,4-tetrahydroisoquinoline
      -3-carboxylic acid
<220> FEATURE:
<221> NAME/KEY: MOD_RES
<222> LOCATION: (7)..(7)
<223> OTHER INFORMATION: AMIDATION

<400> SEQUENCE: 41

Tyr Xaa Trp Phe Tyr Pro Ser
1               5

<210> SEQ ID NO 42
<211> LENGTH: 7
<212> TYPE: PRT
<213> ORGANISM: synthetic construct
<220> FEATURE:
<221> NAME/KEY: MOD_RES
<222> LOCATION: (2)..(2)
<223> OTHER INFORMATION: Xaa is Tic, i.e. 1,2,3,4-tetrahydroisoquinoline
      -3-carboxylic acid
<220> FEATURE:
<221> NAME/KEY: MOD_RES
<222> LOCATION: (4)..(4)
<223> OTHER INFORMATION: Phe is Phe(pNO2), i.e. 4-nitrophenylalanine
<220> FEATURE:
<221> NAME/KEY: MOD_RES
<222> LOCATION: (7)..(7)
<223> OTHER INFORMATION: AMIDATION

<400> SEQUENCE: 42

Tyr Xaa Trp Phe Tyr Pro Ser
1               5

<210> SEQ ID NO 43
<211> LENGTH: 7
<212> TYPE: PRT
<213> ORGANISM: synthetic construct
<220> FEATURE:
<221> NAME/KEY: MOD_RES
<222> LOCATION: (2)..(2)
<223> OTHER INFORMATION: Xaa is Tic, i.e. 1,2,3,4-tetrahydroisoquinoline
      -3-carboxylic acid
<220> FEATURE:
<221> NAME/KEY: MOD_RES
<222> LOCATION: (6)..(6)
<223> OTHER INFORMATION: Nle
<220> FEATURE:
<221> NAME/KEY: MOD_RES
<222> LOCATION: (7)..(7)
<223> OTHER INFORMATION: AMIDATION

<400> SEQUENCE: 43

Tyr Xaa Phe Phe Leu Leu Asp
1               5

<210> SEQ ID NO 44
<211> LENGTH: 3
<212> TYPE: PRT
<213> ORGANISM: synthetic construct
<220> FEATURE:
<221> NAME/KEY: MOD_RES
<222> LOCATION: (2)..(2)
<223> OTHER INFORMATION: Xaa is Tic, i.e. 1,2,3,4-tetrahydroisoquinoline
      -3-carboxylic acid

<400> SEQUENCE: 44
```

Tyr Xaa Phe
1

<210> SEQ ID NO 45
<211> LENGTH: 3
<212> TYPE: PRT
<213> ORGANISM: synthetic construct
<220> FEATURE:
<221> NAME/KEY: MOD_RES
<222> LOCATION: (2)..(2)
<223> OTHER INFORMATION: Xaa is Tic, i.e. 1,2,3,4-tetrahydroisoquinoline
    -3-carboxylic acid
<220> FEATURE:
<221> NAME/KEY: MOD_RES
<222> LOCATION: (3)..(3)
<223> OTHER INFORMATION: AMIDATION

<400> SEQUENCE: 45

Tyr Xaa Phe
1

<210> SEQ ID NO 46
<211> LENGTH: 3
<212> TYPE: PRT
<213> ORGANISM: synthetic construct
<220> FEATURE:
<221> NAME/KEY: MOD_RES
<222> LOCATION: (2)..(2)
<223> OTHER INFORMATION: Xaa is Tic-psi-[CH2-], i.e. 3-methyl-1,2,3,4
    -tetrahydroisoquinolin
<220> FEATURE:
<221> NAME/KEY: MOD_RES
<222> LOCATION: (2)..(3)
<223> OTHER INFORMATION: nonpeptidyl bond

<400> SEQUENCE: 46

Tyr Xaa Phe
1

<210> SEQ ID NO 47
<211> LENGTH: 4
<212> TYPE: PRT
<213> ORGANISM: synthetic construct
<220> FEATURE:
<221> NAME/KEY: MOD_RES
<222> LOCATION: (2)..(2)
<223> OTHER INFORMATION: Xaa is Tic-psi-[CH2-], i.e. 3-methyl-1,2,3,4
    -tetrahydroisoquinolin
<220> FEATURE:
<221> NAME/KEY: MOD_RES
<222> LOCATION: (2)..(3)
<223> OTHER INFORMATION: nonpeptidyl bond

<400> SEQUENCE: 47

Tyr Xaa Phe Phe
1

<210> SEQ ID NO 48
<211> LENGTH: 5
<212> TYPE: PRT
<213> ORGANISM: synthetic construct

<400> SEQUENCE: 48

Tyr Gly Gly Phe Met
1               5

<210> SEQ ID NO 49
<211> LENGTH: 6
<212> TYPE: PRT

-continued

```
<213> ORGANISM: synthetic construct

<400> SEQUENCE: 49

Tyr Gly Gly Phe Met Lys
1               5

<210> SEQ ID NO 50
<211> LENGTH: 6
<212> TYPE: PRT
<213> ORGANISM: synthetic construct

<400> SEQUENCE: 50

Tyr Gly Gly Phe Leu Lys
1               5

<210> SEQ ID NO 51
<211> LENGTH: 6
<212> TYPE: PRT
<213> ORGANISM: synthetic construct
<220> FEATURE:
<221> NAME/KEY: MOD_RES
<222> LOCATION: (1)..(1)
<223> OTHER INFORMATION: NH2 of Tyr is blocked by butyloxycarbonyl group

<400> SEQUENCE: 51

Tyr Gly Gly Phe Leu Lys
1               5

<210> SEQ ID NO 52
<211> LENGTH: 6
<212> TYPE: PRT
<213> ORGANISM: synthetic construct
<220> FEATURE:
<221> NAME/KEY: MOD_RES
<222> LOCATION: (1)..(1)
<223> OTHER INFORMATION: NH2 of Tyr is blocked by butyloxycarbonyl group
<220> FEATURE:
<221> NAME/KEY: MOD_RES
<222> LOCATION: (6)..(6)
<223> OTHER INFORMATION: polymer connected to epsilon-amino group

<400> SEQUENCE: 52

Tyr Gly Gly Phe Leu Lys
1               5
```

We claim:

1. A method for delivering an enkephalin across a blood brain barrier of a subject, comprising administering to the subject an amphiphilic enkephalin-oligomer conjugate, wherein the conjugate has the formula:

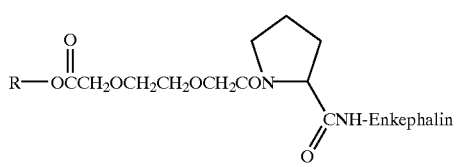

or the formula:

wherein R=alkyl$_{1-26}$, cholesterol, or adamantine.

2. The method of claim 1 wherein the enkephalin is a peptide having the amino acid sequence of SEQ ID NO: 48.

3. The method of claim 1 wherein the enkephalin is a peptide having the amino acid sequence of SEQ ID NO: 49.

4. The method of claim 1 wherein the enkephalin is a peptide having the amino acid sequence of SEQ ID NO: 50.

5. The method of claim 1 wherein the enkephalin is an enkephalin peptide having a proline residue at the N-terminus of the enkephalin peptide.

6. The method of claim 5 wherein the oligomer is coupled to the proline residue at the N-terminus of the alanine residue.

7. The method of claim 1 wherein the enkephalin is an enkephalin peptide having an alanine residue at the N-terminus of the enkephalin peptide.

8. The method of claim 7 wherein the oligomer is coupled to the alanine residue at the N-terminus of the enkephalin peptide.

9. The method of claim 1 wherein the lipophilic moiety is coupled to the hydrophilic moiety by a non hydrolyzable bond.

10. The method of claim 1 wherein the amphiphilic enkephalin-oligomer conjugate is administered as a component of a pharmaceutical composition comprising the enkephalin-oligomer conjugate and a pharmaceutically acceptable carrier.

11. The method of claim 10 wherein the pharmaceutical composition is formulated for oral delivery.

12. The method of claim 10 wherein the pharmaceutical composition is formulated for intravenous delivery.

13. The method of claim 1 wherein the amphiphilic enkephalin-oligomer conjugate is administered as a component of a pharmaceutical composition comprising:

the amphiphilic enkephalin-oligomer conjugate, wherein the enkephalin is an enkephalin peptide having a proline or alanine residue at the N-terminus of the enkephalin peptide;

an amphiphilic enkephalin-oligomer conjugate, wherein the enkephalin is an enkephalin peptide devoid of a proline and alanine residue at the N-terminus of the enkephalin peptide; and a pharmaceutically acceptable carrier.

14. The method of claim 1 wherein the amphiphilic enkephalin-oligomer conjugate is administered by a route selected from the group consisting of intradermal, intramuscular, intraperitoneal, subcutaneous, intranasal, and epidural routes.

15. The method of claim 1 wherein the amphiphilic enkephalin-oligomer conjugate is administered orally.

16. The method of claim 1 wherein the amphiphilic enkephalin-oligomer conjugate is administered intravenously.

* * * * *